US009125384B2

(12) United States Patent
Ishikawa et al.

(10) Patent No.: US 9,125,384 B2
(45) Date of Patent: Sep. 8, 2015

(54) MOUSE HAVING HUMAN LEUKEMIC STEM CELL AND LEUKEMIC NON-STEM CELL AMPLIFIED THEREIN, AND METHOD FOR PRODUCTION THEREOF

(75) Inventors: Fumihiko Ishikawa, Kanagawa (JP); Yoriko Saito, Kanagawa (JP); Osamu Ohara, Kanagawa (JP); Leonard D. Shultz, Bar Harbor, ME (US)

(73) Assignees: RIKEN, Wako (JP); The Jackson Laboratory, Bar Harbor, ME (US)

(*) Notice: Subject to any disclaimer, the term of this patent is extended or adjusted under 35 U.S.C. 154(b) by 881 days.

(21) Appl. No.: 12/738,559

(22) PCT Filed: Oct. 17, 2008

(86) PCT No.: PCT/JP2008/068892
§ 371 (c)(1),
(2), (4) Date: Sep. 24, 2010

(87) PCT Pub. No.: WO2009/051238
PCT Pub. Date: Apr. 23, 2009

(65) Prior Publication Data
US 2011/0307964 A1 Dec. 15, 2011

(30) Foreign Application Priority Data
Oct. 18, 2007 (JP) ................................. 2007-271870

(51) Int. Cl.
*A01K 67/00* (2006.01)
*A01K 67/027* (2006.01)
*A61K 49/00* (2006.01)
*A61K 39/395* (2006.01)
*G01N 33/50* (2006.01)
*G01N 33/569* (2006.01)
*G01N 33/574* (2006.01)

(52) U.S. Cl.
CPC ........ *A01K 67/0271* (2013.01); *G01N 33/5088* (2013.01); *G01N 33/56972* (2013.01); *G01N 33/57426* (2013.01); *A01K 2207/20* (2013.01); *A01K 2217/15* (2013.01); *A01K 2227/105* (2013.01); *A01K 2267/0331* (2013.01)

(58) Field of Classification Search
CPC .................... A01K 67/0271; G01N 33/57426; G01N 33/5088; G01N 33/56972
USPC .......................................................... 800/8
See application file for complete search history.

(56) References Cited

U.S. PATENT DOCUMENTS 7,259,290 B1 * 8/2007 Miyakawa et al. ............. 800/21
8,541,033 B2 * 9/2013 Ito et al. ........................ 424/577

FOREIGN PATENT DOCUMENTS

| JP | WO/2004/040970 A1 * | 5/2004 |
| JP | 2004-154058 A | 6/2004 |
| JP | 2006-271376 A | 10/2006 |
| JP | 2007-531494 A | 11/2007 |
| WO | WO 2005/007892 A1 | 1/2005 |
| WO | WO/2006/039678 A2 * | 4/2006 |

OTHER PUBLICATIONS

Kawano et al., 2005, Leukemia 19:1384-1390.*
Askenasy et al., 2003, Biol. Blood and Marrow Transplantation 9:496-504.*
El-Ouriaghli et al 2003, Blood 102:3786-3792.*
van Rhenen et al May 2007, Leukemia 21:1700-1707.*
Ailles et al., *Blood*, 90(7): 2555-2564 (Oct. 1, 1997).
Agliano et al., *Int. J. Cancer*, 123(9): 2222-2227 (2008).
Bonnet et al., *Nature Medicine*, 3(7): 730-737 (1997).
Cao et al., *Immunity*, 2: 223-238 (Mar. 1995).
Christianson et al., *The Journal of Immunology*, 158: 3578-3586 (1997).
Dewan et al., *Journal of Virology*, 77(9): 5286-5294 (May 2003).
Feuring-Buske et al., *Leukemia*, 17: 760-763 (2003).
Huntly et al., *Cancer Cell*, 6: 587-596 (2004).
Ishikawa et al., *Blood*, 106(5): 1565-1573 (2005).
Jordan et al., *Oncogene*, 23: 7178-7187 (2004).
Hope et al., *Nature Immunology*, 5(7): 738-743 (2004).
Hosen et al., *Proc. Natl. Acad. Sci. USA*, 104(26): 11008-11013 (Jun. 26, 2007).
Lapidot et al., *Nature*, 367: 645-648 (Feb. 17, 1994) (Abstract).
Lumkul et al., *Leukemia*, 16: 1818-1826 (2002).
Nakamura et al., *British Journal of Haematology*, 130: 51-57 (2005).
Passegue et al., *Proc. Natl. Acad. Sci. USA*, 100(Suppl. 1): 11842-11849 (Sep. 30, 2003).
Shultz et al., *The Journal of Immunology*, 154: 180-191 (1995).
Shultz et al., *The Journal of Immunology*, 164: 2496-2507 (2000).
Shultz et al., *The Journal of Immunology*, 174: 6477-6489 (2005).
Shultz et al., *Transplantation*, 76(7): 1036-1042 (Oct. 15, 2003).
Van Rhenen et al., *Blood*, 110(7): 2659-2666 (2007).
Japanese Patent Office, Notice of Reasons for Refusal in Japanese Patent Application No. 2009-538174 (May 7, 2013).

* cited by examiner

Primary Examiner — Robert M Kelly
Assistant Examiner — Kelaginamane T Hiriyanna
(74) Attorney, Agent, or Firm — Leydig, Voit & Mayer, Ltd.

(57) ABSTRACT

The invention relates to a method of selectively expanding human leukemic cells in a non-adult NOD/SCID/IL2rg$^{null}$ mouse by transplanting a substance containing a leukemic stem cell derived from a human acute myelogenous leukemia patient to the mouse. In addition, the invention relates to screening for a medicament capable of eradicating leukemic stem cell (LSC), consideration of treatment methods suitable for individual patients, identification of a differentially expressed gene and the like, using a mouse with expanded human leukemic cells.

20 Claims, 13 Drawing Sheets

MOUSE HAVING HUMAN LEUKEMIC STEM CELL AND LEUKEMIC NON-STEM CELL AMPLIFIED THEREIN, AND METHOD FOR PRODUCTION THEREOF

TECHNICAL FIELD

The present invention relates to a mouse in which leukemic stem cells (LSC) derived from human acute myelogenous leukemia (AML) patient have been engrafted, and human AML cells are selectively expanded in the bone marrow, spleen and peripheral blood, and a production method thereof. In addition, the present invention relates to screening, using the mouse, for a medicament capable of eradicating LSC, a method of consideration of treatment methods suitable for individual patients and the like. Furthermore, the present invention relates to a method of identifying a marker molecule specific to quiescent human LSC, and the development of an LSC selective therapeutic agent for AML, using the marker molecule as a target.

BACKGROUND ART

Acute myelogenous leukemia (AML) is the most common/highly frequent (onset rate) adult leukemia, characterized by the clonal expansion of immature myeloblasts initiating from rare leukemic stem cells (LSCs) (non-patent documents 1-3). The functional and molecular characteristics of human LSCs are largely undetermined.

While murine leukemia models have provided valuable insights into leukemogenesis, direct in vivo study of primary human leukemia is necessary to understand pathogenic mechanisms unique to human leukemogenesis (non-patent document 4). However, since existing immunodeficient strains such as CB17/SCID (non-patent document 5), NOD/SCID (non-patent documents 6-8) and NOD/SCID/$\beta 2m^{null}$ (non-patent document 9) with short life spans and age-dependent leakiness of humoral immunity make it difficult to achieve a high engraftment rate of primary human AML, and extremely difficult to perform long-term assessment of primary human AML.

Shultz et al. recently developed a novel immunodeficient mouse strain carrying a complete null mutation of the common cytokine receptor γ chain upon the scid background that leads to a lack of both acquired and innate immunity. In addition, we created a novel immunodeficient strain with improved long-term xenogeneic engraftment, NOD.Cg-Prkde$^{scid}$Il2rg$^{tm1 Wjl/J}$(NOD/SCID/IL2rγ$^{null}$) mice, carrying a complete null mutation of the common γ chain (non-patent document 10) (non-patent document 11). This strain, with life expectancy of >90 weeks, is more robust than strains such as NOD/SCID (non-patent document 12), NOD/SCID/$\beta 2m^{null}$ (non-patent document 13), NOD-Rag1$^{null}$ (non-patent document 14) and NOD-Rag1$^{null}$Prf1$^{null}$ (non-patent document 15), allowing assessment of the reconstitution and lymphoid/myeloid differentiation capacity of human long-term repopulating HSCs (LT-HSCs) (non-patent documents 4, 16).

Although conventional chemotherapeutic agents can temporarily remit AML, recurrence later is the difficult problem that prevents us from helping patients. For the development of an effective therapeutic agent or treatment method, elucidation of the recurrence mechanism by clarifying the leukemia features unknown to date is strongly desired. To achieve the goal, the development of an animal model capable of reproducing features of human, rather than mouse, AML, particularly AML of individual patients, rather than a cell line, and permitting long-term assessment is essential.

non-patent document 1: Passegue, E., Jamieson, C. H., Ailles, L. E. & Weissman, I. L. Normal and leukemic hematopoiesis: are leukemias a stem cell disorder or a reacquisition of stem cell characteristics Proc Natl Acad Sci USA 100 Suppl 1, 11842-11849 (2003).

non-patent document 2: Hope, K. J., Jin, L. & Dick, J. E. Acute myeloid leukemia originates from a hierarchy of leukemic stem cell classes that differ in self-renewal capacity. Nat Immunol 5, 738-743 (2004).

non-patent document 3: Jordan, C. T. & Guzman, M. L. Mechanisms controlling pathogenesis and survival of leukemic stem cells. Oncogene 23, 7178-7187 (2004).

non-patent document 4: Huntly, B. J. et al. MOZ-TIF2, but not BCR-ABL, confers properties of leukemic stem cells to committed murine hematopoietic progenitors. Cancer Cell 6, 587-596 (2004).

non-patent document 5: Lapidot, T. et al. A cell initiating human acute myeloid leukaemia after transplantation into SCID mice. Nature 367, 645-648 (1994).

non-patent document 6: Bonnet, D. & Dick, J. E. Human acute myeloid leukemia is organized as a hierarchy that originates from a primitive hematopoietic cell. Nat Med 3, 730-737 (1997).

non-patent document 7: Ailles, L. E., Gerhard, B. & Hogge, D. E. Detection and characterization of primitive malignant and normal progenitors in patient with acute myelogenous leukemia using long-term coculture with supportive feeder layers and cytokines. Blood 90, 2555-2564 (1997).

non-patent document 8: Lumkul, R. et al. Human AML cells in NOD/SCID mice: engraftment potential and gene expression. Leukemia 16, 1818-1826 (2002).

non-patent document 9: Feuring-Buske, M. et al. Improved engraftment of human acute myeloid leukemia progenitor cells in beta 2-microglobulin-deficient NOD/SCID mice and in NOD/SCID mice transgenic for human growth factors. Leukemia 17, 760-763 (2003).

non-patent document 10: Cao, X. et al. Defective lymphoid development in mice lacking expression of the common cytokine receptor gamma chain. Immunity 2, 223-238 (1995).

non-patent document 11: Ishikawa, F. et al. Development of functional human blood and immune systems in NOD/SCID/IL2 receptor {gamma} chain(null) mice. Blood 106, 1565-1573 (2005).

non-patent document 12: Shultz, L. D. et al. Multiple defects in innate and adaptive immunologic function in NOD/LtSz-scid mice. J Immunol 154, 180-191 (1995).

non-patent document 13: Christianson, S. W. et al. Enhanced human CD4+ T cell engraftment in beta 2-microglobulin-deficient NOD-scid mice. J Immunol 158, 3578-3586 (1997).

non-patent document 14: Shultz, L. D. et al. NOD/LtSz-Rag1null mice: an immunodeficient and radioresistant model for engraftment of human hematolymphoid cells, HIV infection, and adoptive transfer of NOD mouse diabetogenic T cells. Journal of Immunology 164, 2496-2507 (2000).

non-patent document 15: Shultz, L. D. et al. NOD/LtSz-Rag1nullPfpnull mice: a new model system with increased levels of human peripheral leukocyte and hematopoietic stem-cell engraftment. Transplantation 76, 1036-1042 (2003).

non-patent document 16: Shultz, L. D. et al. Human lymphoid and myeloid cell development in NOD/LtSz-scid IL2R gamma null mice engrafted with mobilized human hemopoietic stem cells. J Immunol 174, 6477-6489 (2005).

DISCLOSURE OF THE INVENTION

Problems to be Solved by the Invention

It is therefore an object of the present invention to provide a superior model mouse of human AML, elucidate the recurrence mechanism of AML by using this mouse, and develop a therapeutic agent or treatment method suitable for AML.

Means of Solving the Problems

In view of the above-mentioned problems, we have conducted intensive studies, and firstly clarified that NOD/SCID/IL2rgKO mouse supports higher engraftment rates of leukemia than NOD/SCID/b2mKO mouse considered most superior among conventional immunodeficient mice. Furthermore, we have shown that transplantation in neonate stages supports significantly higher engraftment rates than in mature stages adopted by many researchers for technical conveniences. In addition, the present inventors have found that a mouse obtained by transplanting an LSC-containing substance derived from a human acute myelogenous leukemia (AML) patient into a neonate NOD/SCID/IL2rg$^{null}$ mouse sufficiently reproduces AML pathology of each human patient and is suitable as a model mouse of AML, and that human AML cells (LSC and non-LSC) can also be expanded by successive transplantation from mouse to mouse. Furthermore, an analysis of the mouse has clarified homing of LSC to osteoblastic-rich region in the bone marrow (BM) and engraftment of LSC therein, and clarified that the cell cycle of LSC is discontinued at the quiescent stage, whereby LSC is protected from apoptosis induced by a cell cycle-dependent chemotherapeutic agent. Therefore, the present inventors performed comprehensive analyses of gene expression profiles of human LSC, extracted a gene that showed different expression in LSC wherein the cell cycle stopped in the quiescent stage, and identified the gene as an LSC marker gene.

The present inventors have conducted further studies based on these findings and completed the present invention.

Accordingly, the present invention provides the following:
(1) a method of producing a mouse having selectively expanded human leukemic cells, comprising transplanting a substance containing a leukemic stem cell derived from a human acute myelogenous leukemia patient into a non-adult NOD/SCID/IL2rg$^{null}$ mouse, and raising the mouse;
(2) a method of producing a mouse having selectively expanded human leukemic cells, comprising one or more repeats of a step of transplanting a substance containing a leukemic stem cell derived from the mouse obtained by the method of the above-mentioned (1) into a different non-adult NOD/SCID/IL2rg$^{null}$ mouse and raising the mouse;
(3) the method of the above-mentioned (1) or (2), wherein the raising period after transplantation of the substance is not less than 4 weeks;
(4) the method of any of the above-mentioned (1) to (3), wherein the human leukemic cell is expanded in the mouse peripheral blood;
(5) the method of any of the above-mentioned (1) to (4), which reproduces the pathology of leukemia in the patient from whom the substance is derived;
(6) a mouse having selectively expanded human leukemic cells, which is obtained by the method of any of the above-mentioned (1) to (4);
(7) a method of screening for a therapeutic agent for human acute myelogenous leukemia, comprising a) a step of administering a test substance to the mouse of the above-mentioned (6) and b) a step of assessing improvement in leukemia in the mouse;
(8) the method of the above-mentioned (7), further comprising c) a step of monitoring a side effect of the test substance in the mouse;
(9) a method of selecting or optimizing a method of treating a patient from whom leukemic cells in the peripheral blood of the mouse of the above-mentioned (6) are derived, comprising a) a step of providing the mouse with a treatment of human acute myelogenous leukemia, and b) a step of assessing an improvement and/or a side effect caused by the treatment of leukemia in the mouse;
(10) the method of any of the above-mentioned (7) to (9), comprising examining the peripheral blood collected from the mouse in step b) and/or step c);
(11) a method of identifying a human leukemic stem cell marker gene, comprising a) a step of comprehensively detecting gene expressions in hCD34$^+$hCD38$^+$ cell and hCD34$^+$hCD38$^-$ cell isolated from a human acute myelogenous leukemia patient and the mouse of the above-mentioned (6), and hCD34$^+$hCD38$^+$ cell and hCD34$^+$hCD38$^-$ cell isolated from normal human cord blood, bone marrow and humanized mouse, and b) a step of identifying a gene expressed differentially between the normal and leukemia hCD34$^+$hCD38$^+$ cell and hCD34$^+$hCD38$^-$ cell;
(12) the method of the above-mentioned (11), wherein the marker gene is a quiescent human leukemic stem cell marker gene;
(13) a therapeutic agent for acute myelogenous leukemia comprising an antibody to a quiescent human leukemic stem cell marker molecule, wherein the cell is targeted;
(14) a method of treating acute myelogenous leukemia, comprising administering, to a patient, an antibody to a quiescent human leukemic stem cell marker molecule;
(15) an antibody to a quiescent human leukemic stem cell marker molecule, which is for treating acute myelogenous leukemia.

Effects of the Invention

The mouse obtained by the present invention is particularly superior as a human AML model, since human AML cells alone are selectively expanded and normal hematopoietic stem cells and the like are not expanded. In addition, since human AML cells are remarkably expanded not only in the bone marrow and spleen but also in the peripheral blood, the progress can be observed alive without sacrificing the mouse. Moreover, since the mouse can well reproduce the characteristics (profile of protein expressed on cell surface, gene expressed by cell and the like) of individual AML patients from whom the transplanted LSC-containing substance is derived, the mouse is effective in that the effectiveness of a therapeutic drug or a treatment method can be monitored and the recurrence of AML can be predicted early. On the other hand, since the human LSC marker molecule (quiescent stage) of the present invention can be a molecular target effective for LSC resistant to conventional chemotherapeutic agents, it enables the development of novel anti-LSC treatment strategy.

BRIEF DESCRIPTION OF THE DRAWINGS

[FIG. 1-2] (c-j) Representative flow cytometric analyses of AML patient BM and corresponding primary, secondary and tertiary recipients PB and BM (c, e, g and i: AML M2 and d, f, h and j: AML M4). (c, d) hCD34 and hCD38 expression in primary AML BM was analyzed (left panels). From the rectangular gate indicated, 10$^3$, 10$^4$ and 10$^5$ hCD34$^+$hCD38$^-$ BM cells were sorted for primary transplantation. The majority of patient BM cells expressed the myeloid markers hCD13 or hCD33 (middle and right panels). (e, f) Primary recipient PB engraftment was measured at weeks 4, 8, 12 and 16 post-injection and showed dose-dependency (left panels). Primary recipient BM engraftment and hCD34 and hCD38 expression was examined at 16 weeks post-injection and 10$^4$ sorted primary recipient BM hCD34$^+$hCD38$^-$ cells were injected into secondary recipients (middle and right panels). (g, h) Secondary recipient PB engraftment was measured every 2-3 weeks between weeks 4 and 18 (left panels). Secondary recipient BM engraftment and hCD34 and hCD38 expression was examined at 18 weeks post-transplantation and cells were sorted from each rectangular gate shown for tertiary transplantation (middle and right panels). (i, j) Sorted secondary recipient BM hCD34$^+$hCD38$^-$ (8×10$^3$, n=2), hCD34$^+$hCD38$^+$(5×10$^4$, n=2) and hCD34$^-$ (2×10$^6$, n=2) AML M2), and BM hCD34$^+$hCD38$^-$ (10$^3$, n=1), hCD34$^+$hCD38$^+$(6×10$^3$, n=1) and hCD34$^-$ (10$^5$, n=1) (AML M4) were injected into tertiary recipients. PB engraftment was measured every 2 weeks between weeks 4 and 20 post-transplantation. Tertiary recipient BM engraftment and hCD34 and hCD38 expression were examined at 20 weeks post-transplantation.

[FIG. 2-1] Normal murine hematopoiesis is suppressed following human LSC homing and engraftment in the BM osteoblast-rich area. (a) Representative PB flow cytometric analyses of hCD34$^+$hCD38$^-$ LSC recipient using antibodies against human and murine erythroid and platelet markers (AML M4 secondary recipient PB at 12 weeks post-transplantation). All mature erythrocytes and platelets are of murine origin. (b) Both PB hemoglobin concentration and platelet count declined with increasing PB human AML burden in secondary recipients of 10$^4$ sorted hCD34$^+$hCD38$^-$ BM cells OWL M2, n=3; AML M4, n=2) and in tertiary recipients of 10$^3$ sorted hCD34$^+$hCD38$^-$ BM cells (AWL M2, filled squares, n=2; AML M4, open circles, n=1). (c) When compared with those of a non-transplanted control mouse, femur and spleen of tertiary-transplanted recipient of sorted hCD34$^+$hCD38$^-$ AML M2 BM cells at 18 weeks post-transplantation show suppression of erythropoiesis.

[FIG. 2-2] (d) Immunohistochemical analyses of femoral sections of newborn mice injected with sorted hCD34$^+$thCD38$^-$ AML M2 and M4 primary BM cells following high dose (6-8 Gy) irradiation, at 3 days post-injection using anti-hCD34 antibody. The majority of endogenous murine leukocytes in the BM cavity are eradicated by irradiation. Significant homing/engraftment of hCD34$^+$ cells is not seen in the center of the BM cavity. In contrast, hCD34$^+$ AML cells are present preferentially at the metaphyseal endosteal regions (arrow heads). (e) Immunohistochemical analyses using anti-hCD34 and anti-hCD38 antibodies at 16 weeks post-transplantation. There is a preferential localization of hCD34$^+$ cells in the endosteal compared with the central region (arrow heads), while hCD38$^+$ cells are sparse in the endosteal compared with the central region.

[FIG. 2-3] (f) (Upper panel) In 4 independent samples, the hCD34$^+$ cells were enumerated within the endosteal and the central areas of the BM, showing that nearly all homed hCD34$^+$ cells are located in the endosteum (* p<0.0001, two-tailed t test). (Middle and lower panels) In 3 independent samples, hCD34 or hCD38 positive cells were enumerated within the endosteal and the central areas of the BM, showing that a large majority of hCD34$^+$ cells reside within the endosteal region and nearly all hCD38$^+$ cells are located in the central region (*, ** p<0.0001, two-tailed t test).

[FIG. 3-1] Primary hCD34$^+$hCD38$^-$ LSCs within the endosteal region exhibit relative resistance to Ara-C induced apoptosis in an in vivo therapeutic testing model. (a) (Left panel) A single 150 mg/kg dose of Ara-C was administered i.p. 12-16 weeks post-primary transplantation to recipients of sorted hCD34$^+$CD38$^-$ BM cells (AML M2, open squares, n=2; AML M4, open circles, n=2; AML M4, filled circles, n=2). Following Ara-C injection on day 0, hCD45$^+$hCD33$^+$ cell count per ml of PB was monitored every four days, showing a rapid decline in AML burden in the engrafted mice resulting in the nadir of AML count at 8-12 days followed by AML count recovery by days 28-32. (+) indicates that the mouse has died. (Right panels). Adverse effect of Ara-C was examined in vivo. Typical hematologic adverse effects of Ara-C were seen in Ara-C-treated AML-engrafted mice at day 8 after i.p. injection. One mouse also developed a mild elevation of AST, a hepatic aminotransferase, at day 8 after injection. (b) (Left) At day 3 after Ara-C injection, BM hCD45$^+$ cell fractions from AML-engrafted mouse were examined for the extent of apoptosis (n=3). Two sets of dot plots are shown. (Right) The hCD34$^+$hCD38$^-$ cells exhibit a relative resistance to Ara-C compared with hCD34$^+$hiCD38$^-$ and hCD34$^-$ populations (p<0.05, two-tailed t test). Open circle, filled circle and open square represent independent samples. (c) Femoral bone sections were obtained in untreated AML-engrafted and AML M2-engrafted mice at day 3 post-Ara-C injection. In the untreated femur, the BM space is packed with uniform-appearing AML blasts (upper panels). At day 3 after Ara-C treatment, there is a decrease in cellularity in the BM space except at the endosteal surface of the bone (middle panels). TUNEL staining confirms the preferential killing of cells in the middle of the BM cavity while the cells at the endosteal surface are relatively spared (lower panels).

[FIG. 3-2] (d) Immunohistochemical analyses of femoral bone section using anti-hCD34 and anti-hCD38 antibodies showing that hCD34$^+$hCD38$^-$ cells remain in the endosteal region after chemotherapy. (e) Immunofluorescence staining of femoral bone section using anti-hCD34 (red) and anti-murine osteopontin (green) antibodies and DAPI (blue)

shows that hCD34⁺ AML cells remain at the endosteal surface abutting murine osteoblasts at day 3 after Ara-C injection. Similar findings are observed by immunohistochemical staining by anti-hCD34 (pink) and anti-murine osteopontin (brown) antibodies. (f) Cell cycle status of LSCs and non-stem cell fractions in AML-engrafted recipients were analyzed by BrdU incorporation and Hoechst/Pyronin Y staining. (Left) A representative set of plots is shown. (Right) The majority of hCD34⁺hCD38⁻ LSCs is in the $G_0$ phase (* $p=0.004$ and ** $p=0.001$, two-tailed t test).

Figure 4:
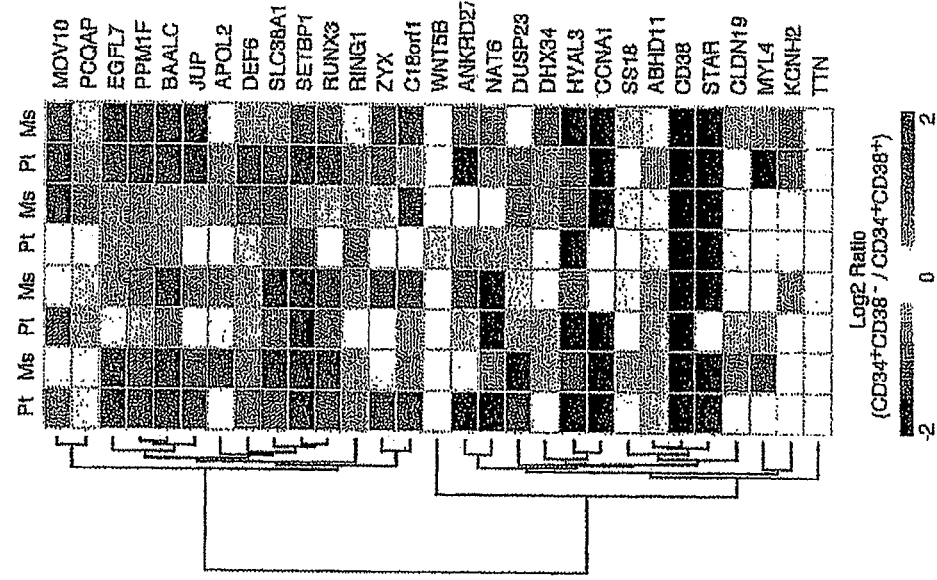
Figure 4:
Figure 4:
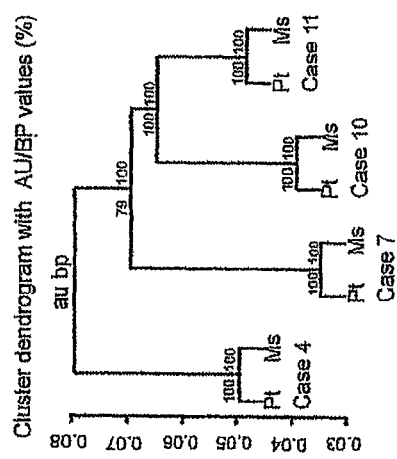

[FIG. 4] Global gene expression profiling of primary human AML and recipient mouse BM identifies LSC-specific transcripts. (a) Comparison of the comprehensive gene expression profiles between hCD34⁺hCD38⁻ cells derived from patient (Pt) and the corresponding recipient mice AML BM (Ms). This panel shows unsupervised hierarchical clustering using correlation distance and average linkage with assessing the uncertainty in clustering by multiscale bootstrap resampling. The numbers at respective branches of the tree represent two types of p-values: approximately unbiased p-value (AU, red) and bootstrap probability value (BP, green). (b) Top six gene sets enriched in hCD34⁺hCD38⁻ cells are represented. False discovery rate (FDR) and nominal p-values of each gene set were calculated based on normalized gene set enrichment score and by permutation of phenotype labels on the samples. (c) Differentially expressed protein-coding genes between CD34⁺CD38⁻ and CD34⁺CD38⁺ cells with statistical significance. Fourteen (MOV10 to C18orf1) and fifteen (WNT5B to TTN) genes were significantly ($p<0.01$) up- and down-regulated, respectively, in CD34⁺ CD38⁻ cells. The color scale indicates a $Log_2$ ratio of the normalized hybridization signal intensities of a differentially expressed gene in CD34⁺CD38⁻ cells to that in CD34⁺CD38⁺ cells. In this panel, red and blue display up- and down-regulation in CD34⁺CD38⁻ cells, respectively, as shown in the reference color code at the bottom of the figure. HUGO Gene Nomenclature Committee-approved gene symbol for each differentially expressed gene identified is shown at the right of each row. The origin of CD34⁺CD38⁺ and CD34⁺CD38⁻ cells [i.e., the case number and either directly from the patient (Pt) or from the xenotransplantation model mouse (Ms)] is shown at the top of each column.

Figure 5:
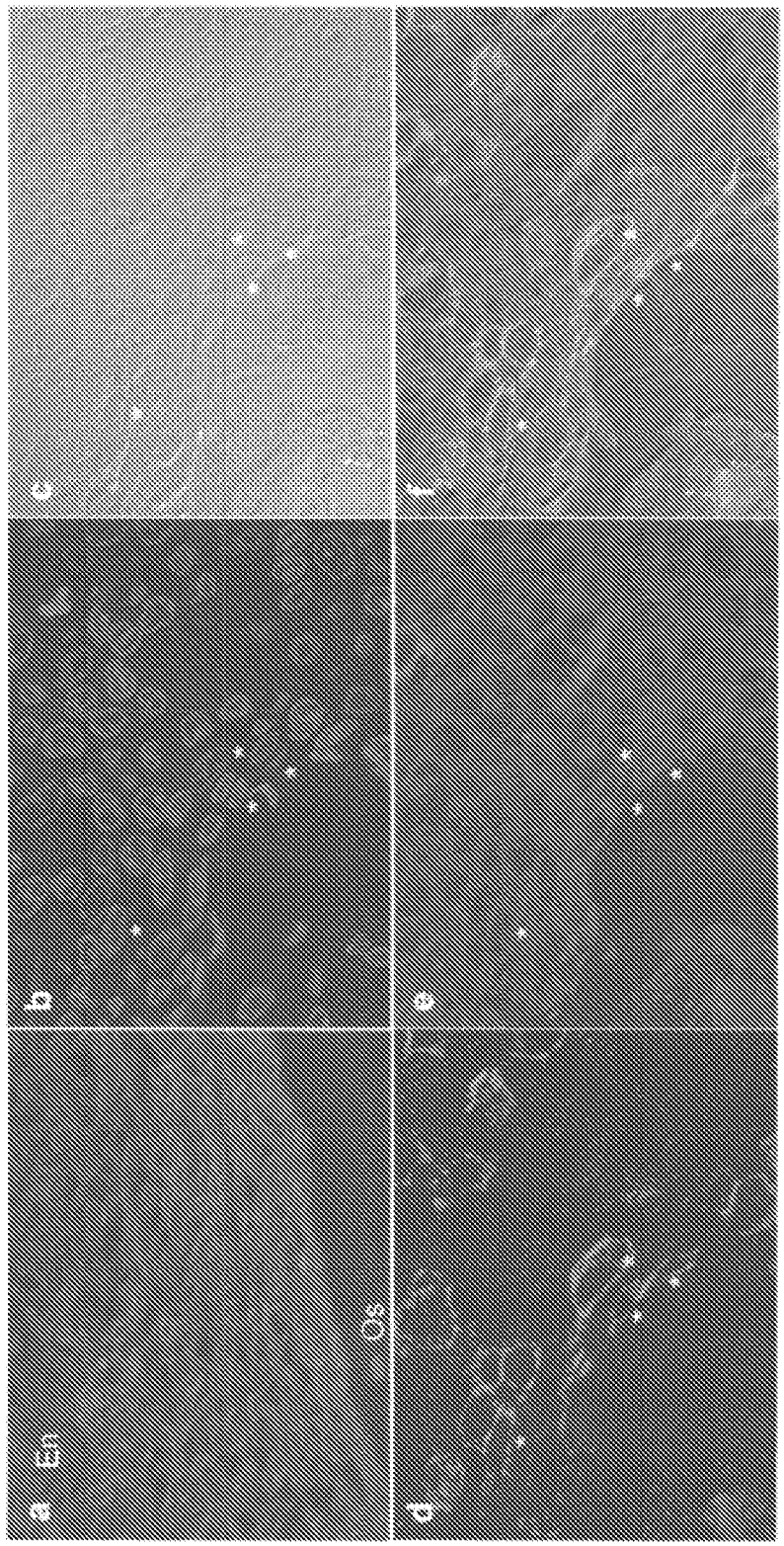

[FIG. 5] (a) Bone sections of AML engrafted mice were labeled with monoclonal mouse anti-human CD45 antibody (red). Nuclei were labeled with DAPI (blue). En: endosteal cell, Os: osteocyte. (b-f) AML-engrafted mouse bone sections were labeled with monoclonal mouse anti-human CD34 antibody (green) and polyclonal goat anti-human CD45 antibody (red). Nuclei were labeled with DAPI (blue).

Figure 6:
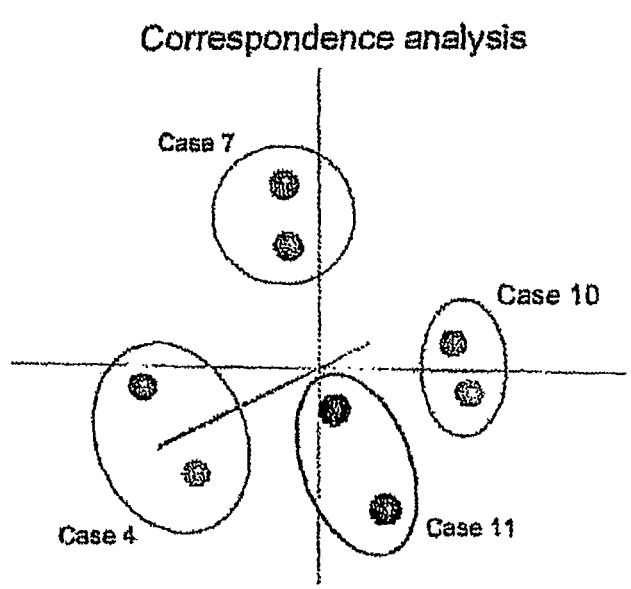

[FIG. 6] Correspondence analysis independently indicating the statistically significant preservation of mRNA profile signatures of patient LSCs after long-term engraftment and serial transplantation in murine recipients.

BEST MODE FOR CARRYING OUT THE INVENTION

The mouse of the present invention having human AML cells selectively expanded in the peripheral blood (to be also referred to as "the mouse of the present invention") can be produced by transplanting a substance containing LSC derived from human AML patient to a non-adult NOD/SCID/IL2rg$^{null}$ mouse, and raising the mouse for a given period or longer. The NOD/SCID/IL2rg$^{null}$ mouse (recipient) to be used for the production method (to be also referred to as "the method of the present invention") can be produced according to the method described in the above-mentioned non-patent document 11. The outline of the specific method is as described in the "material and method" in the Examples to be mentioned later. When used in the present specification, the "non-adult" mouse means a mouse which is 4 weeks old or less, preferably 1 week old or less, more preferably within 3 days after birth (to be also referred to as a "neonate" mouse). The recipient mouse is preferably subjected to irradiation of radiation and the like prior to cell transplantation, so as to kill the bone marrow cells of its own. The recipient mouse to be used is desirably in raising management under conditions with SPF grade or above.

In the present specification, the "substance containing LSC" to be transplanted to the above-mentioned recipient mouse means a cell mixture containing at least LSC harvested from the bone marrow of a human AML patient or an LSC-containing fraction isolated therefrom. The sex, age, disease stage, the kind of AML and the like of the AML patient are not particularly limited and, for example, the AML may belong to any subtype of the French-American-British (FAB) classification system. A substance containing LSC may be, for example, T cell-depleted myelogenic uninuclear cell (TCD-BMMNC) or a hCD34⁺ cell fraction derived from the bone marrow, with particular preference given to hCD34⁺hCD38⁻ cell fraction and the like. These substances containing LSC may contain normal cells (hematopoietic stem cell (HSC) and the like) besides LSC, due to the preparation method thereof. The crude substance containing LSC can be recovered from the bone marrow of an AML patient by a conventional method, various cell fractions containing the LSC can be obtained by flow cytometry and the like using a known cell surface marker molecule. Note that separation of LSC from HSC is difficult.

While the method of transplanting a substance containing LSC to the recipient is not particularly limited, injection, infusion, drip and the like are preferable, and intravenous injection is most preferable. Intrahepatic injection, bone marrow injection and the like also afford engraftment.

After transplantation of a substance containing LSC, the mouse is raised under general raising conditions (preferably SPF conditions or above). As a result, LSC engraftment and expansion of human AML cells are observed in the bone marrow in about 4 weeks, and also in the peripheral blood in about 8 weeks. No particular upper limit is set to the raising period after transplantation, and the mouse can be raised until death. In consideration of the fact that the mouse is subjected to various tests, however, the mouse to be used is desirably 16-week-old or below, preferably 12-week-old or below.

In the mouse of the present invention, remarkable LSC engraftment and AML cell expansion are found not only in the bone marrow (BM) but also in the peripheral blood (PB). In the conventionally-known immunodeficient mice, since AML cells were scarcely detected in the peripheral blood, the mouse of the present invention is the first embodiment providing a convenient and stable AML model system. In the mouse of the present invention, moreover, the presence of a cell derived from a normal human is not confirmed in the peripheral blood. This suggests absence of normal hematopoiesis of human in the recipient mouse. In this sense, AML cell is "selectively" expanded in the peripheral blood of the mouse.

In the present invention, AML cells derived from a human patient are also expanded similarly by collecting a substance containing LSC from the bone marrow of a mouse (primary recipient) directly transplanted with a substance containing LSC derived from a human AML patient, and transplanting the substance to a different non-adult NOD/SCID/IL2rg$^{null}$ mouse (secondary recipient). A similar effect (i.e., selective expansion of AML cell) can also be obtained by repeating the operation in a tertiary recipient, a quaternary recipient and the like (to be referred to as continuous transplantation including that from primary recipient to secondary recipient). The timing of collecting a substance containing LSC from the recipient mouse is preferably, but not limited to, after a sufficient amount of LSC has been engrafted in at least the bone marrow of the mouse, for example, after about 10 weeks, preferably about 12—about 24 weeks, from the transplantation and the like.

When used in the present specification, the "AML cell (also referred to as leukemic cell)" is defined as hCD45$^+$hCD33$^+$ cell and includes hCD34$^+$hCD38$^-$ cell (i.e., chemotherapeutic agent resistant LSC with cell cycle discontinued at quiescent phase, which is selectively capable of developing AML), hCD34$^+$hCD38$^+$ cell (LSC with continued cell cycle), hCD34$^-$ cell (AML non-stem cell) and the like.

The recipient mouse transplanted with leukemic stem cell well reproduces features of human AML such as suppression of normal hematopoiesis (shown by measurement of hemoglobin concentration, platelet count and the like), suppression of red blood cell formation and the like. The expanded AML cell also reproduces, moreover, the features (surface phenotype, form, gene expression pattern and the like of leukemic cell) of the original AML of individual patients such as French-American-British (FAB) classification system, subtypes M0-M7, and the like. Thus, a therapeutic agent/treatment method for AML suitable for each patient can be selected using the recipient mouse as an animal model. Since the NOD/SCID/IL2rg$^{null}$ mouse has a longer life as compared to the mouse lineage used as a conventional AML model, and the system of the present invention also permits continuous transplantation, testing over a longer period of time is possible.

The "mouse of the present invention" can be used for screening for an effective therapeutic agent for AML, selecting/optimizing a treatment method suitable for individual patients, identifying a gene expressed differentially between hCD34$^+$hCD38$^+$ cell and hCD34$^+$hCD38$^-$ cell (i.e., quiescent LSC marker gene) and the like.

To screen for a therapeutic agent for AML, a test substance is administered to the mouse, and the effectiveness (improvement of leukemia) and, where necessary, side effects thereof are assessed. The effectiveness and side effects can be assessed with survival of the mouse, number of AML cells in the bone marrow and the peripheral blood, general status (fur, activity and the like) and the like as indices. Since the mouse of the present invention contains a sufficient amount of AML cells not only in the bone marrow but also in the peripheral blood, the mouse does not need to be killed for collection of the bone marrow, but blood samples from one mouse are sufficient to perform continuous monitoring of the treatment effects and side effects of a test substance. This is the clear superiority when compared to the conventional models. As mentioned above, since the mouse of the present invention has a comparatively long life, the effectiveness and side effects of a test substance can be assessed over a longer period of time.

The administration method of a test substance is not particularly limited, and is appropriately selected from oral administration and parenteral administration (exemplified by, but not limited to, intravenous, intraperitoneal and subcutaneous administrations and the like). The dosage form for the administration is also appropriately determined depending on the administration route, properties of the test substance and the like.

The test substance to be subjected to screening may be any compound or composition and examples thereof include nucleic acids (e.g., nucleoside, oligonucleotide, polynucleotide), carbohydrates (e.g., monosaccharide, disaccharide, oligosaccharide, polysaccharide), lipid (e.g., saturated or unsaturated, straight, branched chain and/or ring-containing fatty acid), amino acid, proteins (e.g., oligopeptide, polypeptide), antibody, organic low-molecular-weight compound, a compound library prepared using a combinatorial chemistry technique, a random peptide library prepared by solid phase synthesis or phage display, natural components (e.g., components derived from microorganism, animals and plants, marine organisms etc.) and the like. The test substance may be a known compound.

One example of a preferable test substance includes an antibody to a known or newly-found AML treatment target molecule, siRNA to a treatment target gene, antisense nucleic acid (DNA, RNA) and the like.

Examples of the method for assessing the effectiveness of a test substance using the peripheral blood include, but are not limited to, time-course monitoring of hCD45$^+$hCD33$^+$ cell count (AML cell count), hemoglobin concentration, platelet count and the like of the peripheral blood. The monitoring can be performed for, for example, about 12-32 weeks after transplantation. Not only effectiveness but also side effects of a test substance may be assessed by such monitoring.

As clarified by the present invention, since AML LSC is present in the bone marrow niche (endosteal surface adjacent to region rich in osteoblast) and in the quiescent stage ($G_0$ stage) of cell cycle, it cannot be eradicated by a standard chemotherapeutic agent (e.g., Ara-C essential for induction of remission and the like), which is considered to be the cause of AML recurrence. Therefore, the screening method of the present invention is expected to afford a therapeutic agent having an action mechanism independent of the cell cycle, and the development of a therapeutic agent capable of completely recovering AML.

Examples of the currently practiced method for AML treatment include chemical therapy, radiation therapy, stem cell transplantation, other drug therapy, biological therapy, a combination thereof and the like. Since the mouse of the present invention is engrafted with LSC retaining the characteristics of AML of the patient, a treatment method for individual patients can be selected/optimized by subjecting the mouse of the present invention to such AML treatment (one or plural therapies), and assessing the effectiveness (improvement of leukemia) and/or side effects thereof. The "selection/optimization" of a treatment method refers to selection, combination, change of conditions and the like of a therapy suitable for the disease types of individual patients. The method of assessing the effectiveness and/or side effects of the AML treatment is, for example, a method similar to the above-mentioned methods.

The present invention also provides a method of identifying a human leukemic stem cell marker gene, comprising comprehensively detecting gene expressions in noLmal and AML hCD34$^+$hCD38$^+$ cells and hCD34$^+$hCD38$^-$ cells and comparing them. Normal hCD34$^+$hCD38$^+$ cell and hCD34$^+$hCD38$^-$ cell can be obtained by collecting blood from the cord blood or bone marrow of normal subject, or humanized mouse (not particularly limited as long as it is a immunodeficient mouse transplanted with hematopoietic human cell, for example, the mouse described in WO 2004/110139 and the like), and sorting the blood. In addition, AML hCD34$^+$CD38$^+$ cell and hCD34$^+$hCD38$^-$ cell can be obtained in the same manner from AML patient or the mouse of the present invention. Since sampling of human is limited, it is highly useful to employ the mouse of the present invention.

For example, an AML cell marker gene can be extracted by identifying a gene expressed differentially between normal hCD34$^+$hCD38$^±$ cell (normal human HSC) and AML hCD34$^+$hCD38$^±$ cell (LSC). Here, by the "expressed differentially" is meant that the expression levels are significantly different between cells (irrespective of increase or decrease of expression in AML cell). Examples of the method of identifying such genes include, but are not limited to, a combination of microarray with an appropriate statistical analysis method (e.g., the method described later in Examples of the present specification) and the like.

In one preferable embodiment, 1) a gene expressed differentially between AML hCD34$^+$hCD38$^+$ cell (active LSC) and hCD34$^+$hCD38$^-$ cell (quiescent LSC) is identified, and 2) a gene expressed differentially between normal hCD34$^+$hCD38$^+$ cell (active HSC) and hCD34$^+$hCD38$^-$ cell (quiescent HSC) is identified. The gene groups identified in 1) and 2) are compared, a gene group commonly expressed differentially between them is removed, and the rest can be extracted as a quiescent human LSC specific marker gene.

The present invention also provides a quiescent LSC selective therapeutic agent for human AML, which uses, as a molecular target, a protein encoded by the quiescent LSC marker gene identified by the above-mentioned method. Preferable examples of the substance capable of targeting the protein include an antibody to the protein. As shown in the Examples below, genes showing significantly increased expression in quiescent LSC as compared to active LSC were identified (see FIG. 4b). The base sequences of these genes are known, and those of ordinary skill in the art can easily clone cDNA of the gene according to a conventional method and obtain a recombinant protein. An antibody to the protein can be produced by using the obtained recombinant protein or a fragment thereof as an antigen and using a well-known antibody preparation technique. In addition, a medicament for suppressing the expression of the gene directly at the transcription or translation level, which is based on shRNA, siRNA, antisense DNA or antisense RNA, can be one of the candidates of the drug discovery.

The antibody may selectively kill quiescent LSC by using ADCC activity or CDC activity, or may be an immunoconjugate of the antibody bound with an anti-cancer substance by a conventional method. Examples of such anti-cancer substance include radioactive nuclide, toxin, various other drugs and the like. Since LSC is in the quiescent phase and is resistant to cell cycle dependent chemotherapeutic agents, an antibody that kills LSC by a different action mechanism is desirable. The antibody to be used is preferably a monoclonal antibody. While the isotype of the antibody is not particularly limited, it is preferably IgG, IgM or IgA, particularly preferably IgG. The antibody is not particularly limited as long as it has at least a complementarity determining region (CDR) to specifically recognize and bind to a target antigen. It may be a complete antibody molecule or, for example, a fragment such as Fab, Fab', F(ab')$_2$ and the like, a conjugate molecule prepared by genetic engineering such as scFv, scFv-Fc, minibody, diabody and the like, or a derivative thereof, which is modified by a molecule and the like having a protein stabilizing action such as polyethylene glycol (PEG) and the like, and the like. In addition, since the antibody is used as a pharmaceutical product to be administered to human, it is an antibody with reduced risk of causing antigenicity by administration to human, specifically, complete human antibody, humanized antibody, mouse-human chimera antibody and the like, particularly preferably a complete human antibody.

Humanized antibody and chimera antibody can be produced by genetic engineering according to a conventional method. While a complete human antibody can also be produced from human-human (or mouse) hybridoma, production using a human antibody producing mouse and a phage display method is desirable, since a large amount of antibody can be provided stably at a low cost. The immune system humanized mouse for which a patent application has already been filed by the present inventors is also one example thereof (see WO 2004/110139). Here, the "humanized mouse" means an immunodeficient mouse transplanted with a hematopoietic human cell.

The above-mentioned antibody or immunoconjugate can be formulated into a preparation as it is or together with a pharmacologically acceptable carrier, diluent or excipient according to a conventional method, and provided in a dosage form suitable for oral or parenteral administration (e.g., intravenous injection).

Examples of the composition for parenteral administration include injection, suppository and the like. Injection encompasses dosage forms of intravenous injection, subcutaneous injection, intradermal injection, muscle injection, drip injection, intraarticular injection and the like. Such injection is prepared by, for example, dissolving, suspending or emulsifying the above-mentioned active ingredient according to a method known per se in an aseptic aqueous or oil liquid generally used for injection. As the aqueous liquid for injection, for example, saline, isotonic solution containing glucose or other auxiliary agent, and the like are used. Suitable solubilizing agents, such as alcohol (e.g., ethanol), polyalcohol (e.g., propylene glycol, polyethylene glycol), nonionic surfactant [e.g., polysorbate 80, HCO-50 (polyoxyethylene (50 mol) adduct of hydrogenated castor oil)] and the like may be used in combination. As the oil liquid, sesame oil, soybean oil and the like are used, and benzyl benzoate, benzyl alcohol and the like may be concurrently used as solubilizing agents. The prepared injection is generally filled in a suitable ampoule. Suppository to be used for rectal administration is prepared by mixing the above-mentioned substance with a normal base for suppository.

While the dose of the above-mentioned pharmaceutical composition varies depending on the age of patient, symptom, administration route and the like, for administration in the form of an injection, for example, about 0.01-30 mg, preferably about 0.1-20 mg, more preferably about 0.1-10 mg, of the antibody is generally administered conveniently to an adult (body weight 60 kg) per day by intravenous injection.

EXAMPLES

The present invention is explained in more detail in the following by referring to Examples below, which are not to be construed as limitative.

(Materials and Methods)

Mice

NOD.Cg-Prkdc$^{scid}$Il2rg$^{tm1Wjl}$/Sz (NOD/SCID/IL2rγ$^{null}$) mice were developed at The Jackson Laboratory by backcrossing a complete null mutation (Shultz, L. D. et al. Multiple defects in innate and adaptive immunologic function in NOD/LtSz-scid mice. J Immunol 154, 180-191 (1995)) at the Il2rg locus onto the NOD.Cg-Prkdc$^{scid}$ (NOD/SCID) strain. NOD.Cg-Prkdc$^{scid}$b2 m$^{tm1Unc}$ (NOD/SCID/β2m$^{null}$) mice were obtained from a research colony maintained at The Jackson Laboratory. Mice were bred and maintained under defined flora with irradiated food and acidified water at the animal facility of RIKEN and at The Jackson Laboratory according to guidelines established by the Institutional Animal Committees at the respective institutions.

Patient Samples

All experiments were performed with prior authorization from the Institutional Review Board for Human Research at RIKEN RCAI. Leukemia cells from AML patient were collected with written informed consent. Samples were derived from AML patient with French-American-British (FAB) classification system subtype M1 (no maturation beyond promyelocytic; Cases 1, 2 and 11), M2 (myeloblastic with maturation; Cases 3, 4, 10), M3 (promyelocytic; Cases 5, 6), M4 (myelomonocytic, Cases 7, 8 and 12) and M7 (megakaryoblastic, Case 9). BMMNCs were isolated using density-gradient centrifugation.

Primary and Serial Xenogeneic Transplantation of Primary AML BMMNCs

For T cell-depleted (TCD) BMMNC transplantation, whole BMMNCs were incubated with mouse anti-hCD3, hCD4, and hCD8 monoclonal antibodies (BD Immunocytometry, San Jose, Calif.), followed by T cell removal with anti-mouse IgG antibody-conjugated immunomagnetic beads (Dynal, Norway). For sorted hCD34$^+$hCD38$^-$ AML cell transplantation, AML patient BMMNCs were labeled with fluorochrome-conjugated mouse anti-hCD34 and anti-hCD38 monoclonal antibodies (BD Immunocytometry, San Jose, Calif.), followed by fluorescence-activated cell sorting using FACSAria (Becton Dickinson, San Jose, Calif.). In order to avoid contamination, doublets were excluded by analysis of FSC/SSC-height and FSC/SSC-width. The purity of hCD3ehCD38$^-$ cells was higher than 98% after sorting. Newborn (within 2 days of birth) and adult (10-12 weeks of age) mice received 100 and 300cGy of total body irradiation, respectively, at 100cGy/min using a $^{137}$Cs-source irradiator, followed by intravenous injection of AMI cells within two hours.

For primary transplantation, 4×10$^6$ TCD-BMMNCs from nine AML patient (Cases 1-9) and 10$^3$, 1-2×10$^4$ or 1-2×10$^5$ purified hCD34$^+$hCD38$^-$ BM AML cells from six AML patient (Cases 1, 4, 7, 10, 11 and 12) were injected into irradiated newborn recipients (total number of recipients=27). TCD-BMMNC-injected primary recipients were evaluated for BM AML engraftment at 3 months post-transplantation (n=9 for each mouse strain injected). Recipients of purified hCD34$^+$hCD38$^-$ cells were evaluated for PB AML engraftment every 4 weeks until 16-24 weeks post-transplantation. At week 16 post-transplantation, primary recipients of 10$^4$ purified hCD34$^+$hCD38$^-$ AML cells from Cases 1, 4, 7, 10 and 11 were sacrificed to obtain BM for secondary transplantation. In each case, 10$^4$-5×10$^5$ hCD34$^4$1$^{-1}$CD38$^-$ cells derived from primary recipient BM were purified by cell sorting and injected into irradiated secondary recipients (the number of AML cases=5, total number of recipients=24). Secondary recipient PB was monitored for AML engraftment, hemoglobin concentration and platelet count at 2-3 week intervals. At 16-24 weeks post-transplantation, secondary recipients of AML cases 4, 7 and 10 were sacrificed to obtain BM for tertiary transplantation. From a Case 4 (AML M2) secondary recipient, sorted BM hCD34$^+$hCD38$^-$ (8×10$^3$), hCD34$^+$hCD38* (5×10$^4$) and hCD34$^-$ (2×10$^6$) cells were injected into irradiated tertiary recipients (n=2 each). From a Case 7 (AML M4) secondary recipient, sorted BM hCD34$^+$hCD38$^-$ (10$^3$), hCD34$^+$hCD38$^+$ (6×10$^3$) and hCD34$^-$ (10$^5$) cells were injected into irradiated tertiary recipients (n=1 each). From a Case 10 (AML M2) secondary recipient, sorted BM hCD34$^+$hCD38$^-$ (10$^4$) cells were injected into irradiated tertiary recipients (n=3). Tertiary recipient PB was monitored for AML engraftment, hemoglobin concentration and platelet counts at 2-4 week intervals until week 16-24. Detailed transplantation results are also shown in Table 1.

PB and BM Analysis of Recipient Mice

BM was harvested from femurs and tibiae and PB was collected from retro-orbital plexus of transplant recipients. Surface phenotypes of BM and PB cells were analyzed by flow cytometry using mouse anti-hCD33, hCD13, hCD34, hCD38, hCD45, hGPA, hCD41a and rat anti-mTer119, and mCD41a monoclonal antibodies (BD Immunocytometry). Engrafted hCD45$^+$hCD33$^+$ cells were sorted and examined morphologically by May-Grunwald Giemsa staining. Human AML engraftment was defined as % hCD45$^+$hCD33$^+$ in recipient BM, since all sorted hCD45$^+$hCD33$^+$ recipient BMMNCs were leukemic blasts as confirmed by May-Grunwald-Giemsa staining.

Histological Analysis of NOD/SCID/IL2r$\gamma^{null}$ Recipient Bone Sections

Paraformaldehyde-fixed, decalcified, paraffin-embedded sections were prepared from femurs of the recipients transplanted with sorted hCD34$^+$hCD38$^-$ AML BM cells. Each section was subjected to hematoxylin and eosin (HE) staining. TUNEL staining was performed according to standard procedures using ApopTag peroxidase in situ apoptosis detection kit (Intergene, Purchase, N.Y.) by Biopathology Institute (Oita, Japan). To determine the localization of the CD34$^+$ cell populations, sections were immunostained with mouse anti-hCD34 antibody (Immunotech, France) and rat anti-mouse osteopontin antibody (Immuno-Biological Laboratories, Tokyo, Japan) were used. For the quantitative localization of LSCs, endosteal and central regions were defined as the zones within or outside twelve cells from the endosteum, respectively, as described previously (Nilsson, S. K., Johnston, H. M. & Coverdale, J. A. Spatial localization of transplanted hemopoietic stem cells: inferences for the localization of stem cell niches. Blood 97, 2293-2299 (2001)). Cell counts within each region were performed under light microscopy using Zeiss Axiovert 200 (Carl Zeiss, Germany). For homing analysis, 4×10$^3$-4×10$^4$ BM hCD34$^+$hCD38$^-$ cells from Cases 4, 7 and 10 were injected into newborn recipients after receiving 6-8 Gy irradiation. The recipients were sacrificed and femurs and tibiae were obtained for histological analyses on day 3. A total of 10,065 cells were counted from femoral and tibial sections. For localization post-engraftment analysis, a total of 24,973 cells were counted using femoral and tibial sections prepared from recipients of BM hCD34$^+$hCD38$^-$ cells from Cases 4, 10 and 11. Immunofluorescence labeling was performed using monoclonal anti-human CD45 antibody (Dako, Denmark) and monoclonal anti-human CD34 antibody (Immunotech). To determine co-localization of hCD34 and hCD45 on surface of leukemic cells, polyclonal goat anti-human CD45 antibody (Santa Cruz Biotechnology, Calif.) was used. Alexa 488-conjugated donkey anti-mouse IgG and Alexa 568-conjugated donkey anti-goat IgG (Invitrogen, CA) were used as secondary antibodies. Laser-scanning confocal imaging was performed using Zeiss LSM 510 (Carl Zeiss, Germany).

Cytosine Arabinoside (Ara-C) Treatment and Analysis

Intraperitoneal (i.p.) injection of 150 mg/kg Ara-C (Biogenesis, Poole, UK) was performed in NOD/SCID/IL2r$\gamma^{null}$ recipients transplanted with 10$^4$ purified BM hCD34$^+$hCD38$^-$ cells from Cases 4 (n=2) and 7 (n=4) at 12-16 weeks post-transplantation. PB was obtained at the time of injection (day 0) and every four days thereafter and MNCs were labeled with mouse anti-hCD45 and anti-hCD33 monoclonal antibodies to determine the fraction of hCD45$^+$hCD33$^+$ cells using flow cytometry. The number of AML cells/ml PB was determined by multiplying the fraction of PB hCD45+CD33+ cells with total PB leukocyte count/ml in each recipient. Hemoglobin concentration, platelet count and plasma aspartate aminotransferase (AST) levels were analyzed prior to and at 8 days after Ara-C administration.

Post-chemotherapy Apoptosis Analysis

NOD/SCID/IL2rγ$^{null}$ recipients transplanted with $10^4$-$10^5$ sorted BM hCD34+hCD38− cells from Cases 4, 7 and 11 at 12-20 weeks post-transplantation were injected with 150 mg/kg Ara-C i.p. At day 3 after injection, BM was analyzed for the presence of apoptotic cells by first dividing the hCD34+hCD38−, hCD34+hCD38+ and hCD34− fractions within the hCD45+ gate and quantifying the viable population in each fraction by Annexin V and 7-amino-actinomycin D (7AAD) staining (BD Immunocytometry, San Jose, Calif.). Annexin V−7AAD− hCD45+hCD34+hCD38− cells were sorted and $10^3$ cells were injected intravenously into irradiated newborn NOD/SCID/IL2rγ$^{null}$ recipients.

Cell Cycle Analysis

For in vivo BrdU incorporation, human AML-engrafted recipient was pulsed with 2 mg BrdU i.p. and BM was analyzed at 24 hours post-injection using FITC BrdU Flow Kit (BD Biosciences, San Diego, Calif.) and hCD34 and hCD38 antibodies as described above. For quantification of cells in $G_0$ phase of cell cycle, human AML-engrafted recipient BM cells were labeled with 5 µg/m2 Hoechst 33342 and 30 µg/ml Pyronin Y followed by surface staining using anti-hCD34 and hCD38 antibodies.

Microarray Analysis

For microarray analysis, 2-5×$10^4$ hCD34+hCD38− and hCD34+hCD38+ cells were purified from AML patient and the tertiary recipient BM using FACSAria. Total RNA was extracted using ISOGEN-LS reagent (Nippon Gene, Toyama, Japan), and RNA integrity was assessed using a Bioanalyzer (Agilent, Santa Clara, Calif., USA). cDNA synthesis, aRNA amplification, biotinylation, and fragmentation were performed with a One-Cycle Target Labeling Kit (Affymetrix, Santa Clara, Calif., USA). Fifteen µg of labeled samples were added to the hybridization cocktail, and hybridized with Human Genome U133 Plus 2.0 GeneChips (Affymetrix) at 45° C. for 16 hours as described in the manufacturer's instructions. Washing and streptavidin-phycoerythrin staining were conducted using a GeneChip Fluidics Station (Affymetrix). Subsequently, the chips were scanned using a GeneChip Scanner 3000 (Affymetrix). The normalized hybridization intensity for each probe set was calculated using the GC-RMA method (Subramanian, A. et al. Gene set enrichment analysis: a knowledge-based approach for interpreting genome-wide expression profiles. Proc Natl Acad Sci USA 102, 15545-15550 (2005)) of the GeneSpring software package (Agilent) at the default setting. The microarray data were subjected to hierarchical clustering analysis using pvclust (Suzuki, R. & Shimodaira, H. Pvclust: an R package for assessing the uncertainty in hierarchical clustering. Bioinformatics (Oxford, England) 22, 1540-1542 (2006)) implemented in R (http://www.r-project.org/) and the Gene Set Enrichment Analysis (Subramanian, A. et al. Gene set enrichment analysis: a knowledge-based approach for interpreting genome-wide expression profiles. Proc Natl Acad Sci USA 102, 15545-15550 (2005)) using "Curated" gene set collection built on February 2007 with the parameters at the default setting. Correspondence analysis using the same mRNA profiles was also performed (Culhane, A. C., Thioulouse, J., Perriere, G. & Higgins, D. G. MADE4: an R package for multivariate analysis of gene expression data. Bioinformatics (Oxford, England) 21, 2789-2790 (2005)). To define genes showing significantly differential expression between CD34+ CD38− and CD34+CD38+ cells, the microarray data were analyzed by statistical t-test with p-value <0.01. In particular, human protein-coding genes in RefSeq collection (http://www.ncbi.nlm.nih.gov/RefSeq/) were considered in this analysis. All the microarray data were deposited to CIBEX, a public gene expression database in Japan (http://cibex.nig.ac.jp/) with an accession ID CBX21.

Statistical Analysis

The differences in mean percent engraftment were analyzed by the non-parametric Friedman two-way analysis of variance using BMDP Statistical Software (SPSS, Chicago, Ill.). The differences in mean percent primary and secondary engraftment of sorted populations were analyzed by the Kruskal-Wallis test (GraphPad Prism, GraphPad, San Diego, Calif.). Two-tailed t test was used for homing and engraftment localization, apoptosis and cell cycle analyses (GraphPad Prism, GraphPad, San Diego, Calif.)

Example 1

Figure 1:
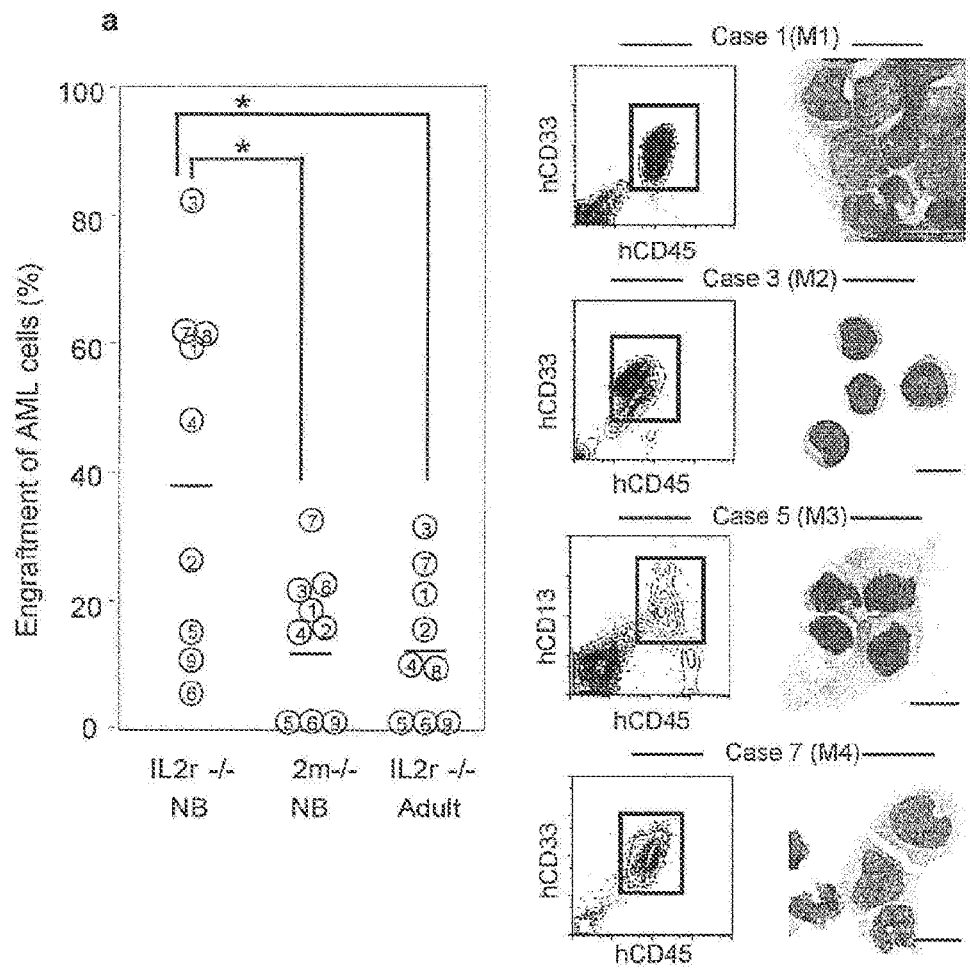
[FIG. 1-1] Phenotypic and functional properties of human primary LSCs are maintained long-term in vivo in NOD/SCID/IL2rγ$^{null}$. (a) (Left) Primary human AML engraftment of NOD/SCID/IL2rγ$^{null}$ newborns, NOD/SCID/γ2m$^{null}$ newborns or NOD/SCID/IL2rγ$^{null}$ adults injected with 4×10$^5$ TCD BMMNCs from nine AML patients. The percentages of human AML (% hCD45$^+$hCD33$^+$ cells) in recipient BM were determined at 3 months post-injection. The number in each circle indicates the case number (Cases 1 and 2: AML M1; Cases 3 and 4: AML M2; Cases 5 and 6: AML M3; Cases 7 and 8: AML M4; Case 9: AML, M7). *p=0.0011 by non-parametric Friedman's test, n=9 for each group. (Right) Surface phenotype and morphology of BM cells from human primary AML recipient NOD/SCID/IL2rγ$^{null}$ mice at 12 weeks post-transplantation compared with normal human BM hCD45$^+$hCD33$^+$ cells. All recipient BM cells expressing both hCD45 and hCD33/hCD13 showed myeloblastic morphology consistent with each original AML type. Scale bar, 5 µm. (b) Percentage AML engraftment in the peripheral blood of recipients of sorted hCD34$^+$hCD38$^-$, hCD34$^+$hCD38$^+$ and hCD34$^-$ BM cells between 16-24 weeks after primary, secondary and tertiary transplantations. In each transplantation cycle, all recipients of sorted BM hCD34+hCD38– cells engrafted while none of the recipients of hCD34+hCD38+ and hCD34– cells showed engraftment (* and **p<0.0001, Kruskal-Wallis test).
Figure 1:
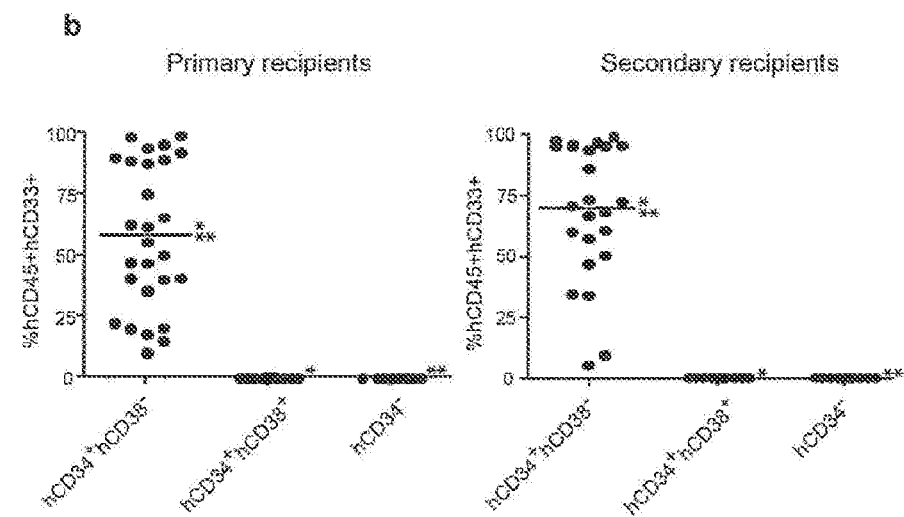

Primary human AML cells engraft with high efficiency in the newborn NOD/SCID/IL2rγ$^{null}$ model. From BM of nine patient containing 80-90% AML blasts, 4×$10^6$ T cell-depleted BM mononuclear cells (BMMNCs) were intravenously injected into sublethally irradiated recipients. Human AML engraftment was significantly more efficient in newborn NOD/SCID/IL2rγ$^{null}$ recipients (37.8%) when compared with adult NOD/SCID/IL2rγ$^{null}$ (11.9%) and newborn NOD/SCID/β2m$^{null}$ (12.9%) recipients (FIG. 1a). Furthermore, all AML patient BMMNCs engrafted in newborn NOD/SCID/IL2rγ$^{null}$ recipients, while 3/9 (two M3 and an M7) BMMNCs failed to engraft in adult NOD/SCID/IL2rγ$^{null}$ and newborn NOD/SCID/β2m$^{null}$ recipients.

Example 2

In CB17/SCID and NOD/SCID mice, human AML hCD34+hCD38− engraftment in BM has been previously demonstrated while limited peripheral blood (PB) engraftment has been detected (Lapidot, T. et al. A cell initiating human acute myeloid leukaemia after transplantation into SCID mice. Nature 367, 645-648 (1994) and Lumkul, R. et al. Human AML cells in NOD/SCID mice: engraftment potential and gene expression. Leukemia16, 1818-1826 (2002)). In the newborn NOD/SCID/IL2rγ$^{null}$ recipients, dose-dependent PB AML engraftment was detected following intravenous injection of as few as $10^3$ sorted primary AML hCD34+ hCD38− cells with no exogenous cytokines or other manipulations, while injection of 5×$10^4$-$10^6$ hCD34+hCD38+ or $10^6$ hCD34− cells did not result in detectable engraftment (FIG. 1b-f; Table 1). Transplanted hCD34+hCD38− LSCs gave rise to hCD45+hCD34+hCD38− cells as well as to hCD45+hCD34+CD38+ and hCD45+hCD34− non-stem AML cells, demonstrating both self-renewal and differentiation capacities of primary LSCs in vivo. In addition to better reproducing primary AML disease in vivo, the presence of circulating PB AML cells allows examination of an individual patient AML over multiple time points in a single recipient. Development, expansion, exacerbation, therapeutic effect and recurrence of AML are all reproduced in the mouse, which is a significant advantage of the newborn NOD/SCID/IL2rγ$^{null}$ model.

Example 3

Serial transplantation demonstrated the functional self-renewal and differentiation capacities of AML BM hCD3e+ hCD38⁻ cells, a defining property of LSCs. In secondary and tertiary recipients, injection of as few as $10^4$ and $10^3$ purified AML BM hCD34⁺hCD38⁻ cells, respectively, resulted in sufficiently efficient long-term engraftment, giving rise to hCD34⁺hCD38⁻ LSCs and hCD34⁺hCD38⁺/hCD34⁻ blasts (FIG. 1b, g-j, Table 1). As in the primary recipients, all secondary and tertiary recipients of sorted hCD34⁺hCD38⁻ cells showed AML engraftment (FIG. 1b, Table 1). In contrast, neither $5\times10^4$-$10^6$ hCD34⁺hCD38⁺ nor $10^5$-$2\times10^6$ hCD34⁻ purified BM cells initiated leukemia detectable in secondary and tertiary recipient PB and BM (FIG. 1b, i, j). These findings demonstrate that LSCs remain hCD34⁺hCD38⁻ while xenogeneic BM microenvironment supports self-renewal and differentiation of human LSCs during the course of serial transplantation. Human AML was maintained cumulatively in vivo from the patient to tertiary recipients for over 1 year, demonstrating the long-term engraftment and self-renewal capacity of LSCs.

TABLE 1

Serial engraftment of sorted hCD34⁺hCD38⁻ AML cells PB % hCD45⁺hCD33⁺ cells were obtained at 16-24 weeks post-transplantation.

| patient | recipient | cell dose | % PB engraftment | average (%) per patient | SEM |
|---|---|---|---|---|---|
| (a) | | | | | |
| 1 (M1) | 1 | 1.0E+04 | 75.1 | N/A | N/A |
| 4 (M2) | 1 | 1.0E+03 | 10.3 | | |
|  | 2 | 1.0E+04 | 40.2 | | |
|  | 3 | 1.0E+05 | 65.5 | 38.7 | 16.0 |
| 7 (M4) | 1 | 1.0E+03 | 20.2 | | |
|  | 2 | 1.0E+03 | 15.0 | | |
|  | 3 | 1.0E+04 | 40.4 | | |
|  | 4 | 1.0E+04 | 55.6 | | |
|  | 5 | 1.0E+04 | 46.9 | | |
|  | 6 | 1.0E+04 | 40.8 | | |
|  | 7 | 1.0E+04 | 50.1 | | |
|  | 8 | 1.0E+04 | 61.7 | | |
|  | 9 | 1.0E+04 | 62.5 | | |
|  | 10 | 1.0E+05 | 95.5 | 48.9 | 7.2 |
| 10 (M2) | 1 | 1.0E+03 | 17.9 | | |
|  | 2 | 1.0E+04 | 90.1 | | |
|  | 3 | 2.0E+05 | 92.3 | | |
|  | 4 | 2.0E+05 | 94.0 | | |
|  | 5 | 2.0E+05 | 98.5 | | |
|  | 6 | 2.0E+05 | 99.1 | 82.0 | 12.9 |
| 11 (M1) | 1 | 1.0E+04 | 20.4 | | |
|  | 2 | 2.0E+04 | 47.0 | | |
|  | 3 | 2.0E+05 | 35.6 | | |
|  | 4 | 2.0E+05 | 22.4 | 31.4 | 6.2 |
| 12 (M2) | 1 | 1.0E+04 | 88.7 | | |
|  | 2 | 1.0E+04 | 87.5 | | |
|  | 3 | 1.0E+04 | 89.2 | 88.5 | 0.5 |
| (b) | | | | | |
| 1 (M1) | 1 | 1.0E+04 | 50.5 | | |
|  | 2 | 1.0E+04 | 60.2 | 55.4 | 4.9 |
| 4 (M2) | 1 | 1.0E+04 | 94.3 | | |
|  | 2 | 1.0E+04 | 73.7 | | |
|  | 3 | 1.0E+04 | 96.1 | | |
|  | 4 | 1.0E+04 | 86.3 | | |
|  | 5 | 1.0E+04 | 60.9 | | |
|  | 6 | 1.0E+04 | 67.3 | | |
|  | 7 | 4.0E+04 | 72.8 | | |
|  | 8 | 4.0E+04 | 57.6 | 76.1 | 5.2 |
| 7 (M4) | 1 | 1.0E+04 | 34.8 | | |
|  | 2 | 1.0E+04 | 34.2 | | |
|  | 3 | 1.0E+04 | 46.9 | | |
|  | 4 | 1.0E+04 | 71.1 | | |
|  | 5 | 4.0E+04 | 95.7 | 56.5 | 11.9 |
| 10 (M2) | 1 | 5.0E+05 | 99.7 | | |
|  | 2 | 5.0E+05 | 68.4 | | |
|  | 3 | 5.0E+05 | 96.5 | | |
|  | 4 | 5.0E+05 | 97.4 | | |
|  | 5 | 5.0E+05 | 95.7 | | |
|  | 6 | 5.0E+05 | 98.2 | | |
|  | 7 | 5.0E+05 | 95.9 | 93.1 | 4.2 |
| 11 (M1) | 1 | 1.0E+04 | 5.5 | | |
|  | 2 | 1.0E+04 | 9.5 | 7.5 | 2.0 |
| (c) | | | | | |
| 4 (M2) | 1 | 8.0E+03 | 45.7 | | |
|  | 2 | 8.0E+03 | 52.1 | | |
|  | 3 | 1.0E+05 | 85.6 | | |
|  | 4 | 1.0E+05 | 75.0 | | |
|  | 5 | 1.0E+05 | 46.5 | | |
|  | 6 | 1.0E+05 | 96.6 | 66.9 | 8.9 |
| 7 (M4) | 1 | 1.0E+03 | 81.3 | N/A | N/A |
| 10 (M2) | 1 | 1.0E+04 | 26.0 | | |
|  | 2 | 1.0E+04 | 36.2 | | |
|  | 3 | 1.0E+04 | 34.7 | | |
|  | 4 | 1.0E+05 | 92.9 | 47.5 | 15.3 |

(a) Primary recipients (n = 27)
(b) Secondary recipients (n = 24)
(c) Tertiary recipients (n = 11)

Example 4

Figures 1, 2:
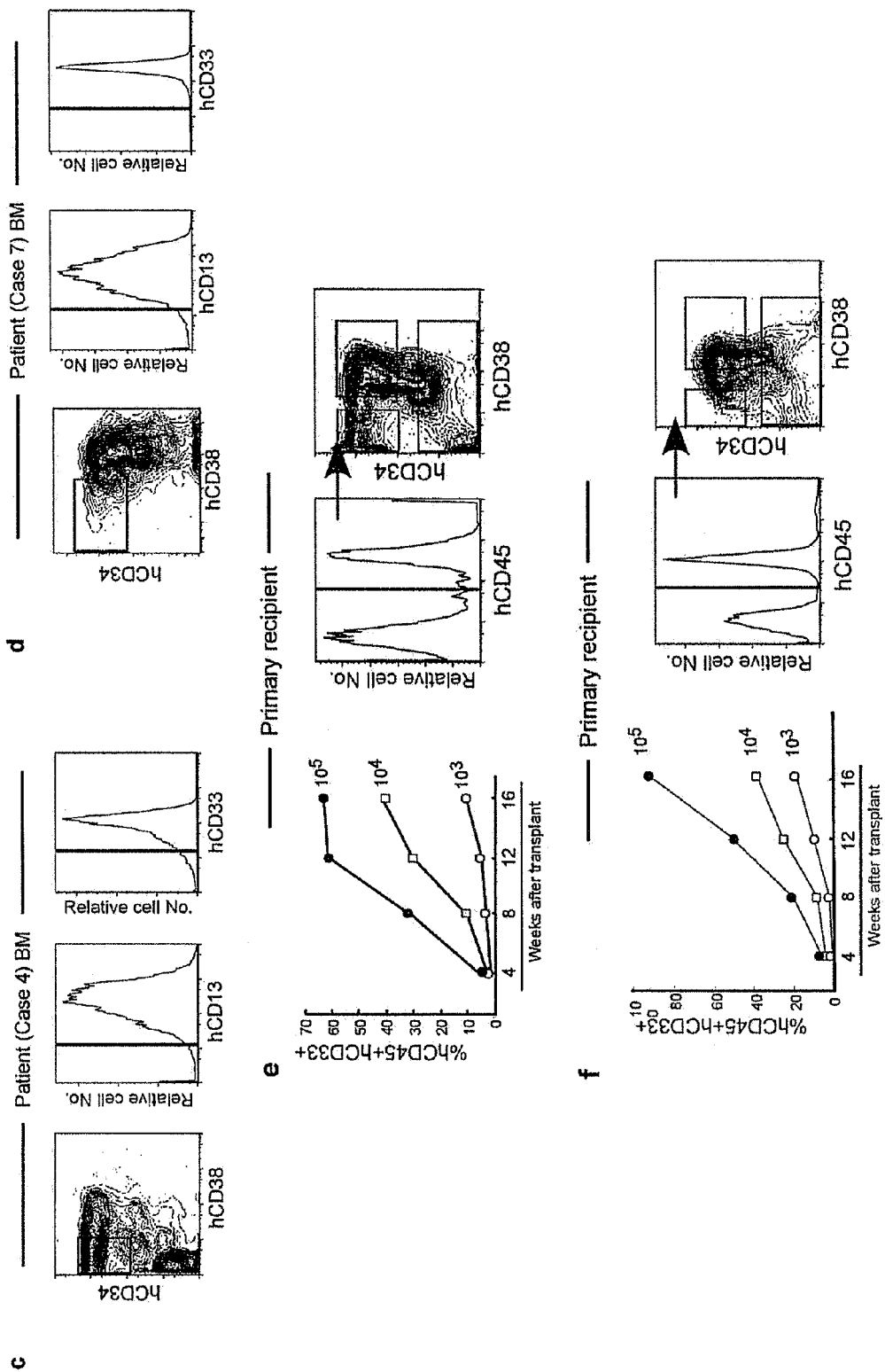
Figures 1, 2:
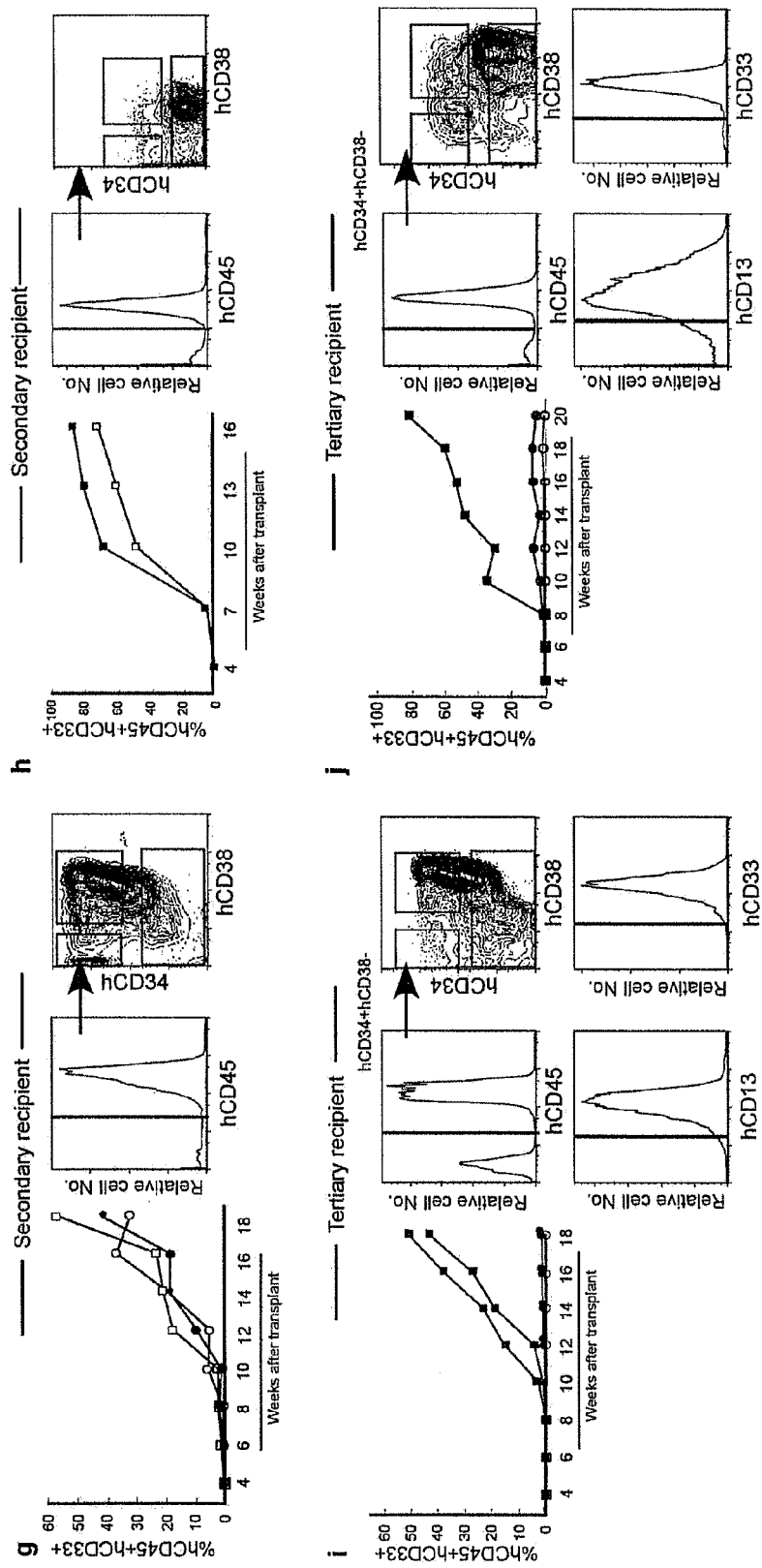

Normal human hematopoiesis was not observed in the course of serial transplantation, and recipient PB erythrocytes and platelets were entirely of murine origin (FIG. 2a). In consideration of the fact that human platelets are produced from only several dozen normal hematopoietic stem cells, this establishes selective engraftment of leukemic stem cells and formation of leukemia in the body of the mouse. Furthermore, recipient PB hemoglobin concentration and platelet counts were inversely proportionate to the leukemic burden, mimicking the suppression of normal hematopoiesis characteristic of AML disease progression (FIG. 2b). Gross appearances of recipient femur and spleen confirmed suppressed erythropoiesis consistent with AML disease (FIG. 2c), findings not observed when sorted hCD34⁺CD38⁺ and hCD34⁻ AML or normal BM hCD34⁺hCD38⁻ cells are transplanted. While recipient spleen size was variable among cases, enlarged spleens consistently contained human AML cells (data not shown). These findings provide additional functional evidence that LSC engraftment and AML expansion in the NOD/SCID/IL2rγ$^{null}$ mouse recapitulates human leukemogenesis.

Example 5

While the microenvironmental niche for human primary (here, since primary means that the cell was directly obtained from the patient, properties of the patient cell are free of an artificial influence by culture and the like) LSCs has not been defined in vivo, the successful long-term engraftment characterized by self-renewal of human LSCs and propagation of differentiated leukemic progeny demonstrates the capacity of NOD/SCID/IL2rγ$^{null}$ mouse BM to provide a supportive microenvironment for human LSC survival and expansion. In other words, even though the environment is not of human but of mouse, this transplantation system has an environment capable of maintaining the functional and cytological characteristics of human leukemic stem cells. To directly locate the microenvironmental niche for LSCs, recipient femoral sections were examined at day 3 following intravenous LSC injection. hCD34+ AML cells were found lining the endosteal surface, the site of the "murine" normal hematopoietic stem cell microenvironmental niche (Zhang, J. et al. Identification of the haematopoietic stem cell niche and m control of the niche size. Nature 425, 836-841(2003); Calvi, L. M. et al. Osteoblastic cells regulate the haematopoietic stem cell niche. Nature 425, 841-846(2003); and Arai, F. et al. Tie2/angiopoietin-1 signaling regulates hematopoietic stem cell quiescence in the bone marrow niche. Cell 118, 149-161 (2004)), while central regions of the BM cavity were nearly acellular and hollow due to irradiation (FIG. 2d). While the cells at the endosteal area are not morphologically uniform, not only the typically round cells but also spindle-shaped and other atypically-shaped cells express CD45, demonstrating that they are human leukemic cells, not endosteal cells or vascular endothelial cells (FIG. 5. a-b). Co-localization of CD45 and CD34 was also confirmed by confocal microscopy imaging (FIG. 5. c-f). hCD34+ AML cells remain preferentially at the endosteal surface abutting murine osteoblasts 4 months after transplantation when BM becomes packed with AML cells, indicating potential interaction between LSCs and osteoblasts (FIG. 2e). Quantitative analysis demonstrated that LSCs homed to and continued to reside within the endosteal areas of the BM (FIG. 2f). As the cells were obtained from AML patient, it is likely that the sorted hCD34+hCD38− cells include normal HSCs as well as LSCs. However, the absence of normal human hematopoietic engraftment in the recipients of sorted hCD34+hCD38− cells indicates that the majority (either numerically or functionally) of these cells are of malignant origin. These findings suggest that the suppression of normal hematopoiesis during AML progression may result from the competition for the shared BM microenvironmental niche.

Example 6

Figures 1, 2:
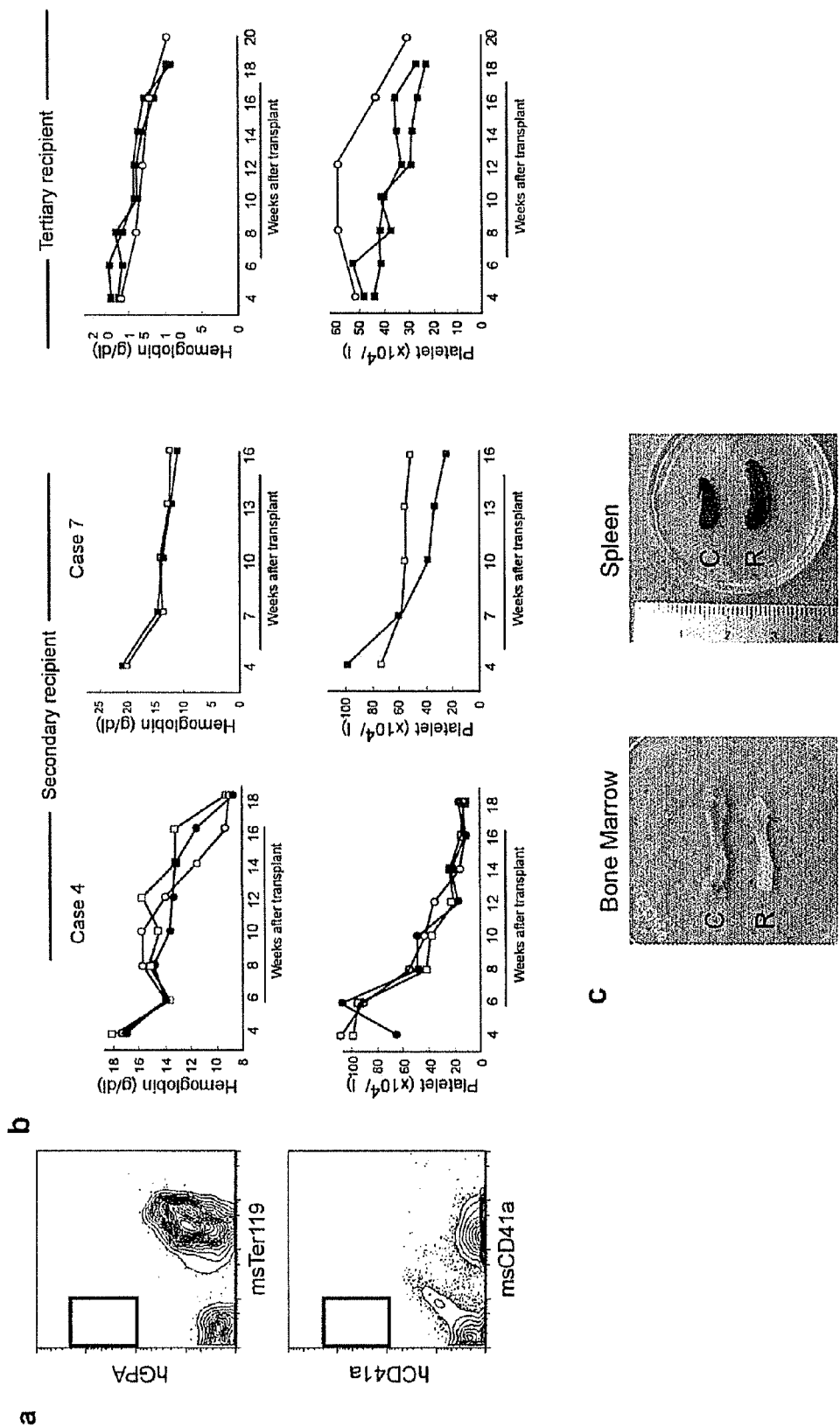
Figure 2:
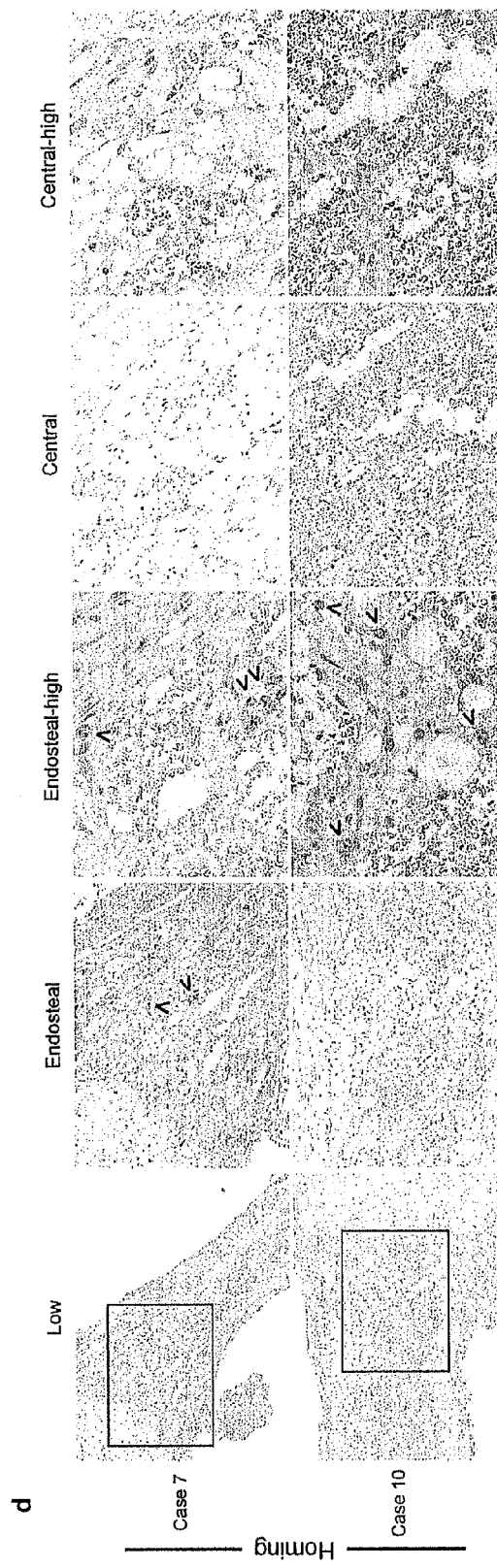
Figure 2:
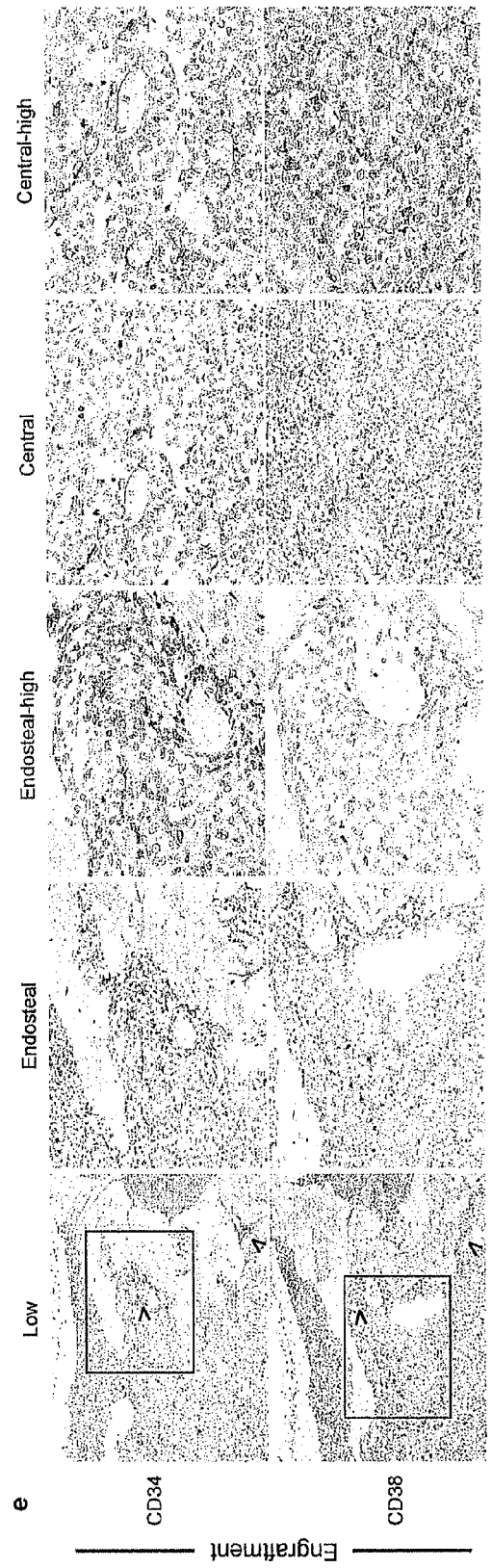
Figures 2, 3:
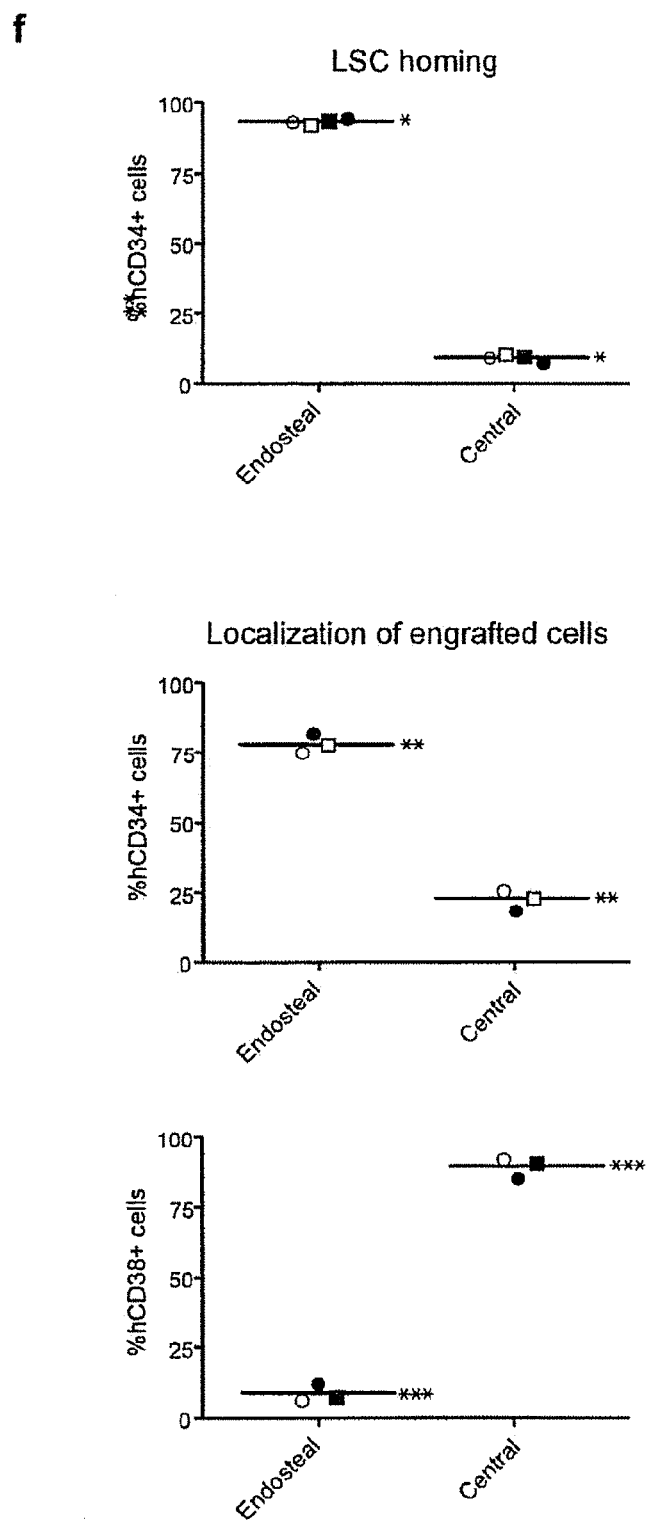
Figures 1, 3:
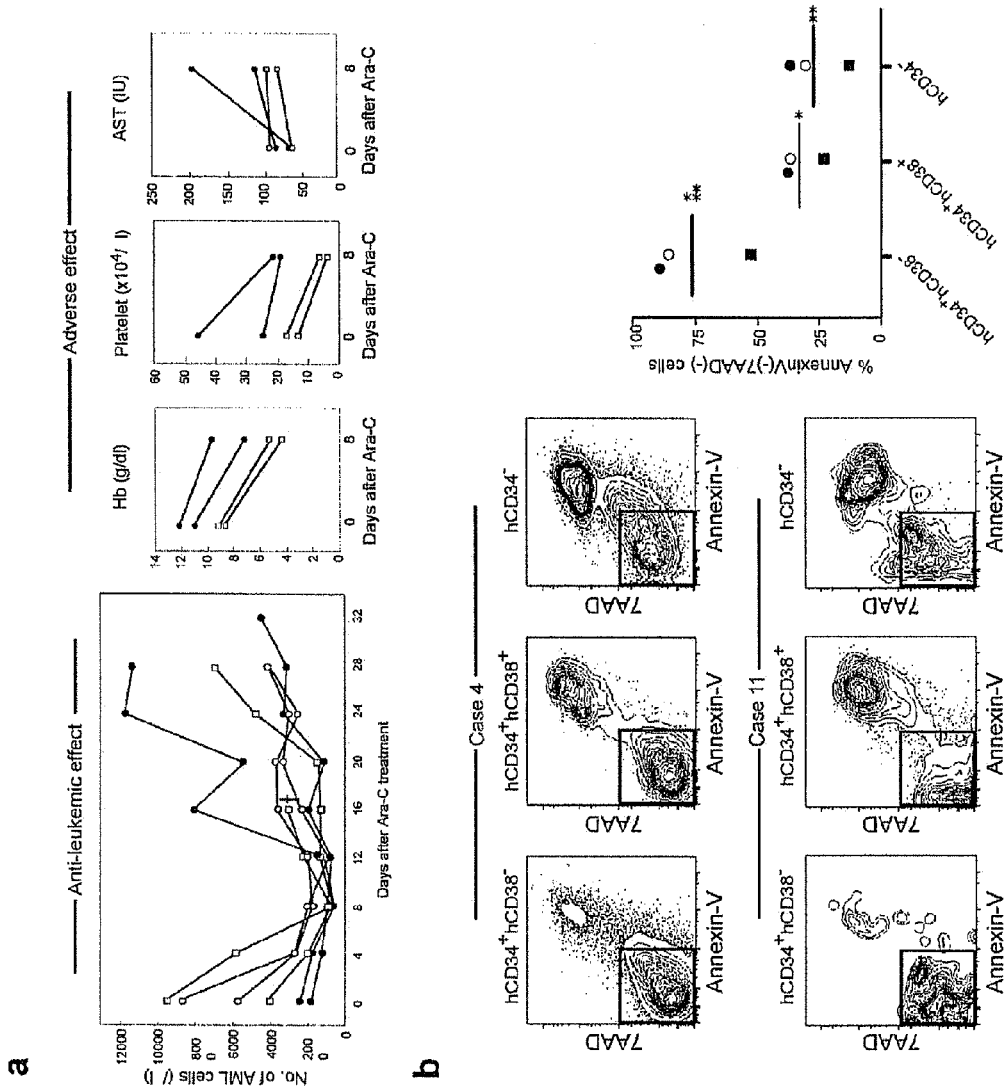
Figures 1, 3:
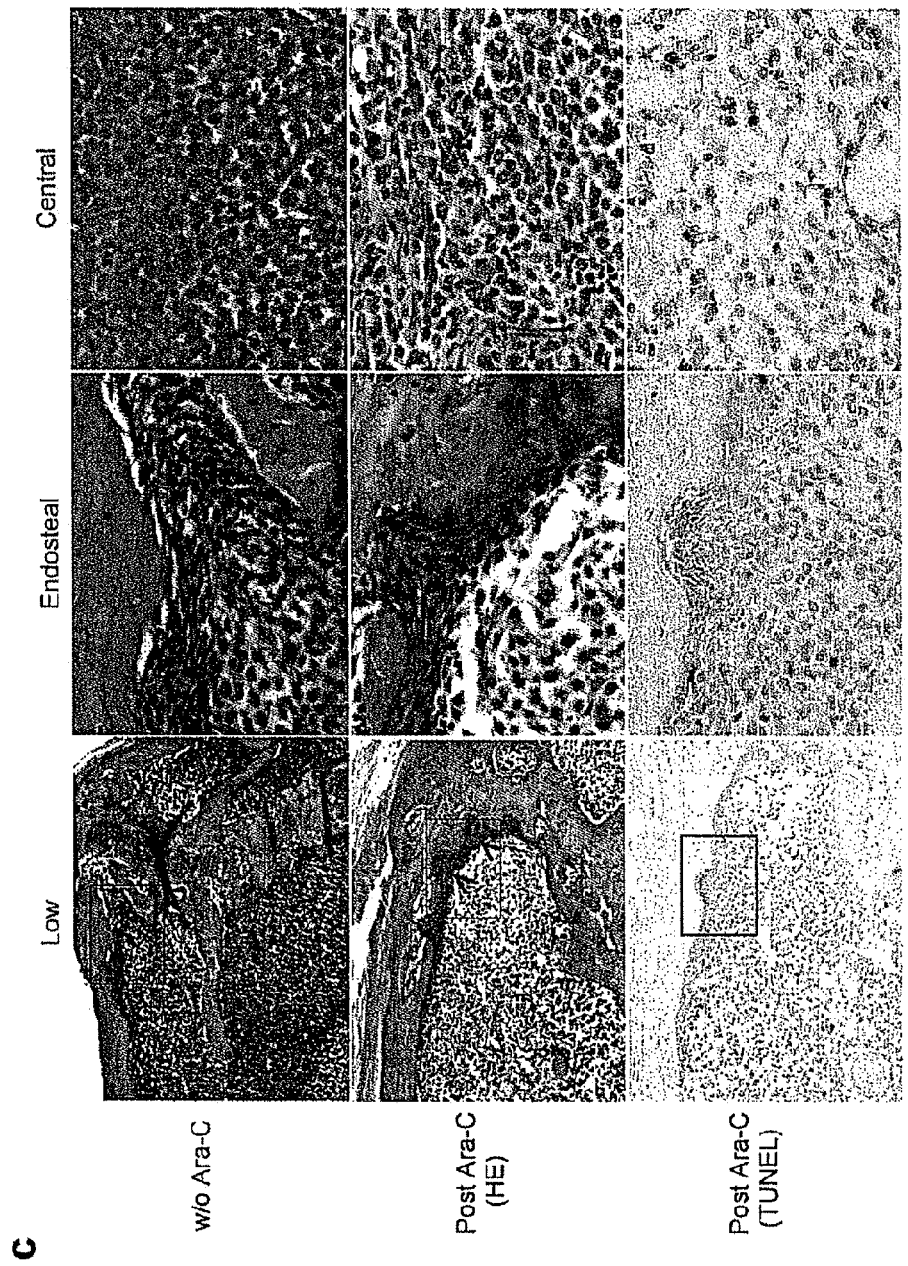
Figures 2, 3:
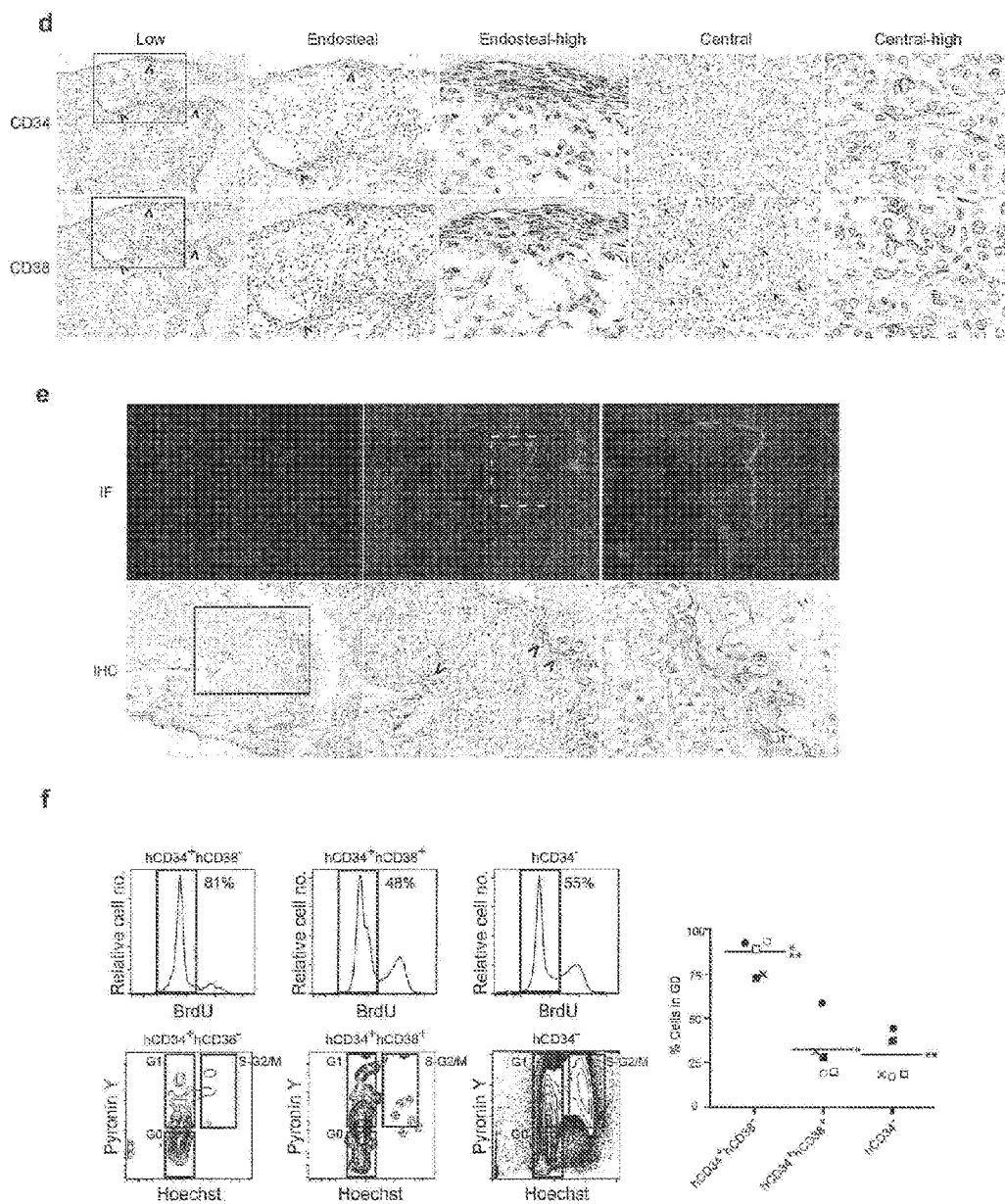

In vivo testing of therapeutic agents can greatly facilitate development of novel therapies for AML and is expected to lead to optimization of therapeutic strategies for individual patient, i.e., realization of personalized medicine (tailor-made medicine). We examined the in vivo anti-leukemic cytotoxicity of cytosine arabinoside (Ara-C) in NOD/SCID/IL2rγ$^{null}$ recipients engrafted with AML (FIG. 3a, left). Cytosine arabinoside is a standard chemotherapeutic agent for the treatment of AML. In Ara-C-treated mice, PB AML burden became markedly reduced by day 8. The cytotoxic effect was accompanied by anemia and thrombocytopenia in all treated mice with mild hepatic toxicity in one animal, consistent with the known toxicity profile of Ara-C (FIG. 3a, right). As is the case in patient with AML, the effect of a single round of Ara-C treatment was transient, followed by AML relapse as demonstrated by the recovery of PB AML cell count by days 16-28.

Example 7

Using this drug-testing model, we examined the chemosensitivity of human AML stem cell and non-stem cell fractions. Flow cytometric analysis of day 3-post-Ara-C BM revealed that the hCD34+CD38− LSCs are more resistant to Ara-C compared to the non-stem AML cell fractions with statistical significance (FIG. 3b). To identify the localization of chemo-resistant leukemic cells, we performed hematoxylin-eosin (HE) and TUNEL staining using day 3 post-Ara-C femoral bone sections. The histological studies demonstrated a marked segregation of apoptotic cells in the center of the bone marrow cavity from TUNEL-negative surviving cells lining the endosteal surface (FIG. 3c). Immunostaining confirmed that the cells abutting endosteum expressed hCD34, but not hCD38, on their surface and were adjacent to osteopontin+ osteoblasts (FIG. 3d,e). Injection of 10$^3$ Annexin V$^-$7AAD$^-$hCD34+hCD38$^-$ cells from Ara-C treated mouse, but not hCD34+hCD38+ or hCD34$^-$ cells, resulted in the development of human AML in secondary recipient, indicating that the chemoresistance of rare LSCs is responsible for AML relapse. As demonstrated by BrdU incorporation and Hoechst/Pyronin Y staining, hCD34+hCD38− AML cells are relatively cell cycle quiescent, compared with the hCD34+hCD38+ and hCD34− cells (FIG. 3f). Since numerous chemotherapeutic agents including Ara-C exert cell cycle dependent cytotoxicity, cell cycle quiescence of LSCs may be one of the mechanisms underlying chemoresistance of LSCs.

Example 8

Since LSCs can exclusively initiate AMI in vivo and are resistant to conventional chemotherapeutic drugs, novel therapeutic strategies specifically targeting chemotherapy-resistant LSCs are needed to prevent disease relapse in human AML (Guzman, M. L. et al. Preferential induction of apoptosis for primary human leukemic stem cells. Proc Natl Acad Sci U S A 99, 16220-16225 (2002); Guzman, M. L. et al. The sesquiterpene lactone parthenolide induces apoptosis of human acute myelogenous leukemic stem and progenitor cells. Blood 105, 4163-4169 (2005); and Taussig, D. C. et al. Hematopoietic stem cells express multiple myeloid markers: implications for the origin and targeted therapy of acute myeloid leukemia. Blood 106, 4086-4092 (2005)). Recently, a cell surface marker, CD44, was reported to be important both in mouse and human LSC homing and engraftment (Jin, L., Hope, K. J., Zhai, Q., Smadja-Joffe, F. & Dick, J. E. Targeting of CD44 eradicates human acute myeloid leukemic stem cells. Nat Med 12, 1167-1174 (2006) and Krause, D. S., Lazarides, K., von Andrian, U. H. & Van Etten, R. A. Requirement for CD44 in homing and engraftment of BCR-ABL-expressing leukemic stem cells. Nat Med 12, 1175-1180 (2006)). In addition to interruption of LSC homing thereby preventing initiation of AML, it is imperative to develop therapies that can eradicate LSCs that have already engrafted and are able to give rise to non-stem AML cells. Comprehensive transcriptome analysis of LSCs compared with non-stem cell fractions in primary ANL patient is a powerful tool to identify such molecular targets specifically expressed in LSCs, at the level of the individual patient. Development of AML model mouse retaining functional property of LSCs can facilitate comprehensive gene profiling by providing LSCs and non-LSCs. Following prospective isolation of functionally defined primary human LSCs from the BM of four primary AML patient and the corresponding four recipient mice, we performed comprehensive gene expression profiling to compare hCD34+hCD38− cells and hCD34+CD38+ cells. High correlation of the gene expression profiles between patient BM-derived hCD34+hCD38− cells and recipient mouse BM-derived hCD34+hCD38− cells indicates that gene expression signatures in LSCs remained relatively stable through serial transplantations in mouse BM microenvironment (FIG. 4a, FIG. 6). This result implicates that the analysis of recipient mouse BM-derived hCD34+hCD38− cells could provide us with complementary information to that of patient BM-derived hCD34+hCD38− cells. Therefore, we performed gene set enrichment analysis to clarify genes that were consistently enriched in hCD34+CD38− compared with hCD34+ hCD38$^+$ cells from each original primary AML BM and the corresponding recipient mouse BM (FIG. 4b). A gene set that was most significantly enriched in LSC fraction was the integrin pathway including genes such as MAPK (mitogen-activated protein kinase), SRC (v-src sarcoma viral oncogene homolog), FYN (FYN oncogene related to SRC, FGR, YES), and PXN (paxillin) (Cursi, S. et al. Src kinase phosphorylates Caspase-8 on Tyr380: a novel mechanism of apoptosis suppression. Embo J 25, 1895-1905 (2006) and Janes, S. M. & Watt, F. M. New roles for integrins in squamous-cell carcinoma. Nat Rev Cancer 6, 175-183 (2006)). Signaling via these integrin-related genes is anti-apoptotic and leads to cell cycle arrest in tumor cells or regulate leukocyte adhesion. Furthermore, we identified genes that are differentially expressed with statistical confidence in LSCs by unsupervised hierarchical clustering (FIG. 4c). Those genes encode transcription factors, negative regulators of apoptosis and transmembrane molecules, potential targets for LSC-specific therapy (FIG. 4c). Relative down-regulation of Cyclin A (CCNA1), which promotes cell cycle from $G_0$ to $G_1$, in LSCs seems to be compatible with the increased % $G_0$ frequency in LSCs as revealed by cell cycle analysis (FIG. 3f). In contrast, BAALC (brain and acute leukemia, cytoplasmic) (Tanner, S. M. et al. BAALC, the human member of a novel mammalian neuroectoderm gene lineage, is implicated in hematopoiesis and acute leukemia. Proc Natl Acad Sci USA 98, 13901-13906 (2001)), whose expression is correlated with poor prognosis of AML patient, is highly expressed in LSCs. Additionally, ring finger protein 1, RING1, which forms polycomb complex through interaction with BMI-1 and acts as a transcriptional repressor, is also overexpressed in LSCs. Comprehensive transcriptome analysis examining larger numbers of AML patients comparing functionally defined populations in NOD/SCID/IL2rγ$^{null}$ mice is required for detection of LSC-specific molecular targets in the future.

Using the NOD/SCID/IL2rγ$^{null}$ primary human AML engraftment model system, we demonstrated that: 1) Long-term engrafting, self-renewing LSCs are present exclusively in AML patient and the recipient mouse BM; 2) LSCs home to, reside within and expand within the osteoblast-rich encloseal area; 3) The majority of LSCs are in $G_0$ phase, and are relatively resistant to Ara-C treatment within the osteoblast-rich area contributing to AML relapse; and 4) LSCs engrafted in mouse BM retain characteristics of patient AML LSCs in phenotype, in function, and in gene expression pattern, enabling the identification of novel LSC-specific therapeutic targets in individual AML patient.

Industrial Applicability

The NOD/SCID/IL2rγ$^{null}$ primary human AML engraftment model may be used for an in vivo determination of the efficacy and optimal therapeutic window for treatment of AML in a patient-specific manner, by creating an abundant source of leukemic cells for in vivo studies from each patient. Prediction of chemosensitivity of primary AML LSCs and evaluation of adverse effects of therapy using an in vivo system will help develop individualized LSC-targeted leukemia treatment. The development of human primary AML-engrafted model that provides functionally defined human LSCs allows isolation of adequate numbers of rare LSCs with non-LSC populations from the recipient mice. The ability to thus expand primary LSCs in vivo enables large-scale molecular analysis of LSC transcriptome, facilitating discovery of therapeutic targets and analysis of drug resistance specific to LSCs for the development of patient-specific LSC-targeted AMI therapy.

This application is based on patent application No. 2007-271870 filed in Japan, the contents of which are encompassed in full herein. In addition, the patent documents and non-patent documents cited in the present specification are hereby incorporated in their entireties by reference, to the extent that they have been disclosed in the present specification.

The invention claimed is:

1. A method of producing a mouse having selectively expanded human acute myelogenous leukemic cells in the peripheral blood, having human leukemic stem cells located in the endosteal surface abutting murine osteoblasts, and suppressing normal hematopoiesis, comprising
   transplanting a substance containing a leukemic stem cell derived from a human acute myelogenous leukemia patient into a NOD/SCID/IL2rγ$^{null}$ mouse that is 4 weeks old or less, and raising the mouse, wherein the raising period after transplantation of the substance is not less than 4 weeks,
   thereby producing a mouse having selectively expanded human leukemic cells including hCD34$^+$hCD38$^-$ cells, and hCD34$^+$hCD38$^+$ cells, and hCD34$^-$ cells in the peripheral blood, having hCD34$^+$hCD38$^-$ cells located in the endosteal surface abutting murine osteoblasts, suppressing normal hematopoiesis, and reproducing the pathology of acute myelogenous leukemia in the patient from whom the substance is derived.

2. A method of producing a mouse having selectively expanded human acute myelogenous leukemic cells in the peripheral blood, having human leukemic stem cells located in the endosteal surface abutting murine osteoblasts, and suppressing normal hematopoiesis, comprising
   one or more repeats of a step of transplanting a substance containing a human leukemic stem cell derived from the bone marrow of a mouse obtained by the method according to claim 1 into a non-transplanted, different NOD/SCID/IL2rγ$^{null}$ mouse that is 4 weeks old or less, and
   raising the mouse, wherein the raising period after transplantation of the substance is not less than 4 weeks,
   thereby producing a mouse having selectively expanded human leukemic cells including hCD34$^+$hCD38$^-$ cells, hCD34$^+$hCD38$^+$ cells and hCD34$^-$ in the peripheral blood, having hCD34$^+$hCD38$^-$ cells located in the endosteal surface abutting murine osteoblasts, suppressing normal hematopoiesis, and reproducing the pathology of acute myelogenous leukemia in the patient from whom the substance is derived.

3. A mouse having selectively expanded human acute myelogenous leukemic cells in the peripheral blood, having human leukemic stem cells located in the endosteal surface abutting murine osteoblasts, and suppressing normal hematopoiesis, which is produced by transplanting a substance containing a leukemic stem cell derived from a human acute myelogenous leukemia patient into NOD/SCID/IL2rγ$^{null}$ mouse that is 4 weeks old or less, and raising the mouse, wherein the raising period after transplantation of the substance is not less than 4 weeks, wherein the raised mouse has selectively expanded human leukemic cells including hCD34$^+$hCD38$^-$ cells, hCD34$^+$hCD38$^+$ cells, and hCD34$^-$ cells in the peripheral blood and hCD34$^+$hCD38$^-$ cells located in the endosteal surface abutting murine osteoblasts, suppressing normal hematopoiesis, and reproducing the pathology of acute myelogenous leukemia in the patient from whom the substance is derived.

4. A method of screening for a therapeutic agent for human acute myelogenous leukemia, comprising a) a step of administering a test substance to the mouse according to claim 3 and b) a step of assessing improvement in leukemia in the mouse.

5. The method according to claim 4, further comprising c) a step of monitoring a side effect of the test substance in the mouse.

6. A method of selecting or optimizing a method of treating a patient from whom leukemic cells in the peripheral blood of the mouse according to claim 3 are derived, comprising a) a step of providing the mouse with a treatment of human acute myelogenous leukemia, and b) a step of assessing an improvement and/or a side effect caused by the treatment of leukemia in the mouse.

7. The method according to claim 4, comprising examining the peripheral blood collected from the mouse in step b).

8. A method of identifying a human leukemic stem cell marker gene, comprising a) a step of comprehensively detecting gene expressions in hCD34$^+$hCD38$^+$ cell and hCD34$^+$hCD38$^-$ cell isolated from a human acute myelogenous leukemia patient and the mouse according to claim 3, and hCD34$^+$hCD38$^+$ cell and hCD34$^+$hCD38$^-$ cell isolated from normal human cord blood, bone marrow and humanized mouse, and b) a step of identifying a gene expressed differentially between the normal and leukemia hCD34$^+$hCD38$^+$ cell and hCD34$^+$hCD38$^-$ cell.

9. The method according to claim 8, wherein the marker gene is a quiescent human leukemic stem cell marker gene.

10. A mouse having selectively expanded human acute myelogenous leukemic cells in the peripheral blood, having human leukemic stem cells located in the endosteal surface abutting murine osteoblasts, and suppressing normal hematopoiesis, which is produced by:
(a) obtaining a substance containing a human leukemic stem cell derived from the bone marrow of the mouse according to claim 3, and
(b) transplanting the substance containing a leukemic stem cell derived from the bone marrow of the mouse of claim 6 into a non-transplanted, different NOD/SCID/IL2rg$^{null}$ mouse that is 4 weeks old or less and raising the different mouse,
wherein the different mouse has selectively expanded human leukemic cells including hCD34$^+$ hCD38$^-$ cells, hCD34$^+$ hCD38$^+$ cells, and hCD34$^-$ cells in the peripheral blood and hCD34$^+$ hCD38$^-$ cells located in the endosteal surface abutting murine osteoblasts, suppressing normal hematopoiesis, and reproducing the pathology of acute myelogenous leukemia in the patient from whom the substance is derived.

11. A method of screening for a therapeutic agent for human acute myelogenous leukemia, comprising a) a step of administering a test substance to the mouse according to claim 10 and b) a step of assessing improvement in leukemia in the mouse.

12. The method according to claim 11, further comprising c) a step of monitoring a side effect of the test substance in the mouse.

13. A method of selecting or optimizing a method of treating a patient from whom leukemic cells in the peripheral blood of the mouse according to claim 10 are derived, comprising a) a step of providing the mouse with a treatment of human acute myelogenous leukemia, and b) a step of assessing an improvement and/or a side effect caused by the treatment of leukemia in the mouse.

14. The method according to claim 5, comprising examining the peripheral blood collected from the mouse in step b) and/or step c).

15. The method according to claim 6, comprising examining the peripheral blood collected from the mouse in step b).

16. The method according to claim 11, comprising examining the peripheral blood collected from the mouse in step b).

17. The method according to claim 12, comprising examining the peripheral blood collected from the mouse in step b) and/or step c).

18. The method according to claim 13, comprising examining the peripheral blood collected from the mouse in step b).

19. A method of identifying a human leukemic stem cell marker gene, comprising a) a step of comprehensively detecting gene expressions in hCD34$^+$hCD38$^+$ cell and hCD34$^+$hCD38$^-$ cell isolated from a human acute myelogenous leukemia patient and the mouse according to claim 10, and hCD34$^+$hCD38$^+$ cell and hCD34$^+$hCD38$^-$ cell isolated from normal human cord blood, bone marrow and humanized mouse, and b) a step of identifying a gene expressed differentially between the normal and leukemia hCD34$^+$hCD38$^+$ cell and hCD34$^+$hCD38$^-$ cell.

20. The method according to claim 19, wherein the marker gene is a quiescent human leukemic stem cell marker gene.

* * * * *